(12) United States Patent
Molteni et al.

(10) Patent No.: US 7,579,363 B2
(45) Date of Patent: Aug. 25, 2009

(54) BICYCLIC COMPOUNDS AND COMPOSITIONS AS PDF INHIBITORS

(75) Inventors: Valentina Molteni, San Diego, CA (US); Xiaohui He, San Diego, CA (US); Yun He, San Diego, CA (US); Andreas Kreusch, San Diego, CA (US); Juliet Nabakka, San Diego, CA (US); Kunyong Yang, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 11/769,679

(22) Filed: Jun. 27, 2007

(65) Prior Publication Data

US 2007/0259852 A1    Nov. 8, 2007

(51) Int. Cl.
*C07D 417/12* (2006.01)
*C07D 279/16* (2006.01)
*A61K 31/5415* (2006.01)

(52) U.S. Cl. ...................................... 514/312; 546/158
(58) Field of Classification Search ................ 546/158; 514/312
See application file for complete search history.

(56) References Cited

OTHER PUBLICATIONS

Ochiai et al. Pharmaceutical Bulletin (1953), 1, 156-60.*
Davis et al. Journal of Medicinal Chemistry, (1964), 7(5), 632-634.*

* cited by examiner

*Primary Examiner*—Kahsay T Habte
(74) *Attorney, Agent, or Firm*—Scott W. Reid; D. Phil; Genomics Institute of the Novartis Research Foundation

(57) ABSTRACT

This invention is directed to novel bicyclic compounds, to the uses of these compounds in various medicinal applications, including treating disorders amenable to treatment by peptidyl deformylase inhibitors such as treatment of bacterial infections, and to pharmaceutical compositions comprising these compounds.

1 Claim, No Drawings

BICYCLIC COMPOUNDS AND COMPOSITIONS AS PDF INHIBITORS

CROSS-REFERENCE TO RELATED APPLICATIONS

This application is a continuation of U.S. patent application Ser. No. 10/903,349, filed Jul. 30, 2004 which claims the benefit of priority to U.S. Provisional Patent Application No. 60/491,765, filed Jul. 31, 2003. The full disclosures of these applications are incorporated herein by reference in their entirety and for all purposes.

BACKGROUND OF THE INVENTION

1. Field of the Invention

This invention is directed to novel bicyclic compounds, to the uses of these compounds in various medicinal applications, including treating disorders amenable to treatment by peptide deformylase inhibitors such as treatment of bacterial infections, and to pharmaceutical compositions comprising of these compounds.

2. Background

Treatment of microbial infection in host organisms requires an effective means to kill the microbe while doing as little harm to the host as possible. Accordingly, agents that target characteristics unique to a pathology-causing microorganism are desirable for treatment. Penicillin is an extremely well known example of such an agent. Penicillin acts by inhibiting biosynthesis of bacterial cell walls. Since mammalian cells do not require cell walls for survival, administration of penicillin to a human infected with bacteria may kill the bacteria without killing human cells. However, the use of antibiotics and antimicrobials has also resulted in increased resistance to these agents. As bacteria become resistant to older, more widely used antimicrobial agents, new antimicrobials must be developed in order to provide effective treatments for human and non-human animals suffering from microbial infection.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins. It has been shown that PDF is required for bacterial growth (Chang et al., J. Bacteriol., Vol. 171, pp. 4071-4072 (1989); Meinnel et al., J. Bacteriol., Vol. 176, No. 23, pp. 7387-7390 (1994); Mazel et al., EMBO J., Vol. 13, No. 4, pp. 914-23 (1994)). Since protein synthesis in eukaryotic organisms does not depend on fMet for initiation, agents that inhibit PDF are attractive candidates for development of new antimicrobial and antibacterial drugs. Prokaryotic organisms, including disease-causing prokaryotes, are described in Balows A, Truper H G, Dworkin M, Harder W and Schleifer K-H (eds.), "The Prokaryotes", 2nd ed., New York: Springer-Verlag Q. (1992); and Holt J G (Editor-in-chief), "Bergey & Apos, S., Manual of Systematic Bacteriology", Vols. 1-4, Baltimore: Williams & Wilkins (1982, 1986, 1989).

PDF is part of the metalloproteinase superfamily. While PDF shares many of the features that characterize metalloproteinases, PDF differs from other members of the superfamily in its secondary/tertiary structure and the metal ions that are coordinated in the active site. Metalloproteinases are critical to many aspects of normal metabolism. The class known as matrix metalloproteinases (MMPs) are involved in tissue remodeling, such as degradation of the extracellular matrix. These enzymes are believed to play a role in normal or beneficial biological events such as the formation of the corpus luteum during pregnancy (see Liu et al., Endocrinology, Vol. 140, No. 11, pp. 5330-5338 (1999)), wound healing (Yamagiwa et al., Bone, Vol. 25, No. 2, pp. 197-203 (1999)), and bone growth in healthy children (Bord et al., Bone, Vol. 23, No. 1, pp. 7-12 (1998)). Disorders involving metalloproteinases have been implicated in several diseases such as cancer, arthritis and autoimmune diseases. Because of the importance of MMPs in normal physiological processes, it would be preferable to develop agents that inhibit PDF, a metalloproteinase present only in prokaryotes, while avoiding significant inhibition of MMPs. Alternatively, PDF inhibitors that also inhibit MMPs may be of use where the therapeutic benefits of inhibiting PDF outweighs the risk of side effects from MMP inhibition.

While a wide variety of compounds have been developed as candidate inhibitors of MMPs and other metalloproteinases, research on inhibitors of PDF is much less extensive. In view of the importance of identifying new antibiotics to treat bacteria resistant to existing antibiotics, it is desirable to develop novel inhibitors of PDF for evaluation and use as antibacterial and antimicrobial agents. The present invention fulfills this need.

SUMMARY OF THE INVENTION

This application relates to compounds of Formula I:

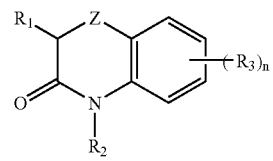

in which:

n is 1, 2 or 3;

Z is selected from —$CH_2$—, —$CH_2CH_2$—, —S—, —S(O)—, —$S(O)_2$— and —$NR_4$—; wherein $R_4$ is selected from hydrogen, hydroxy, halo and $C_{1-4}$alkyl;

$R_1$ is selected from hydrogen, $C_{1-6}$alkyl, —XC(O)$NR_5OR_6$, —$XNR_5COR_6$ and —XC(O)$NR_5R_6$; wherein X is selected from a bond, $C_{1-6}$alkylene, $C_{2-6}$alkenylene and $C_{2-6}$alkynylene; wherein X can be optionally substituted with halo, hydroxy and cyano; $R_5$ is selected from hydrogen, hydroxy and $C_{1-4}$alkyl; and $R_6$ is selected from hydrogen and $C_{1-4}$alkyl;

$R_2$ is selected from hydrogen, $C_{1-12}$alkyl, $C_{2-12}$alkenyl, $C_{2-12}$alkynyl, halo-substituted-$C_{1-12}$alkyl, —$XOR_5$, —$XOR_7$, —XC(O)$OR_5$, —XOC(O)$R_5$, —XC(O)$NR_5R_6$, —XC(O)$NR_5R_7$, —XC(O)$NR_5OR_6$, —$XR_7$, —$XCHR_7R_7$, —XC(O)$R_6$, —$XOXOR_6$, —$XOXOR_7$, —XC(O)$R_7$, —XC≡N, —XC(O)$XR_7$, —$XOXR_7$, —XC(O)$NR_5XR_7$ and —XC(O)$NR_5XNR_5R_6$; wherein X, $R_5$ and $R_6$ are as described above and $R_7$ is selected from $C_{3-10}$cycloalkyl, $C_{5-8}$heterocycloalkyl, $C_{6-10}$aryl and $C_{5-8}$heteroaryl; wherein any cycloalkyl, heterocycloalkyl, aryl or heteroaryl of $R_7$ can be optionally substituted by one to three radicals selected from halo, $C_{1-4}$alkyl, $C_{1-4}$alkoxy, cyano, halo-substituted-$C_{1-4}$alkyl and —XC(O)$OR_5$; wherein X and $R_5$ are as described above; with the proviso that $R_1$ and $R_2$ cannot both be hydrogen; with the proviso that when $R_2$ is not hydrogen when $R_1$ is —$CH_2C(O)$NHOH; with the proviso that $R_1$ and $R_2$ are both not hydrogen;

$R_3$ is selected from hydrogen, halo, $C_{1-6}$alkyl, $C_{1-6}$alkoxy, halo-substituted-$C_{1-6}$alkyl and halo-substituted-$C_{1-6}$alkoxy; and the N-oxide derivatives, prodrug derivatives, individual isomers and mixtures of isomers thereof; and the pharmaceutically acceptable salts and solvates (e.g. hydrates) of such compounds.

A second aspect of the invention is a pharmaceutical composition which contains a compound of Formula I or an N-oxide derivative, individual isomer or mixture of isomers thereof, or a pharmaceutically acceptable salt thereof, in admixture with one or more suitable excipients.

A third aspect of the invention is a method for treating a disease in an animal in which inhibition of PDF activity can prevent, inhibit or ameliorate the pathology and/or symptomology of the disease, which method comprises administering to the animal a therapeutically effective amount of a compound of Formula I or a N-oxide derivative, individual isomer or mixture of isomers thereof; or a pharmaceutically acceptable salt thereof.

A fourth aspect of the invention is the use of a compound of Formula I in the manufacture of a medicament for treating a disease in an animal in which PDF activity contributes to the pathology and/or symptomology of the disease.

A fifth aspect of the invention is a process for preparing compounds of Formula I and the N-oxide derivatives, prodrug derivatives, protected derivatives, individual isomers and mixtures of isomers thereof; and the pharmaceutically acceptable salts thereof

DESCRIPTION OF THE PREFERRED EMBODIMENTS

The invention provides compounds that are useful in the treatment and/or prevention of diseases or disorders mediated by PDF activity. Also provided are methods for treating such diseases or disorders.

Definitions

In this specification, unless otherwise defined:

"Alkyl" as a group and as a structural element of other groups, for example halo-substituted-alkyl, alkoxy, acyl, alkylthio, alkylsulfonyl and alkylsulfinyl, can be either straight-chained or branched. "Alkenyl" as a group and as a structural element of other groups contains one or more carbon-carbon double bonds, and can be either straight-chain, or branched. Any double bonds can be in the cis- or trans-configuration. A preferred alkenyl group is vinyl. "Alkynyl" as a group and as structural element of other groups and compounds contains at least one C≡C triple bond and can also contain one or more C═C double bonds, and can, so far as possible, be either straight-chain or branched. A preferred alkynyl group is propargyl. Any cycloalkyl group, alone or as a structural element of other groups can contain from 3 to 8 carbon atoms, preferably from 3 to 6 carbon atoms. "Alkylene" and "alkenylene" are divalent radicals derived from "alkyl" and "alkenyl" groups, respectively.

"Aryl" means a monocyclic or fused bicyclic aromatic ring assembly containing six to ten ring carbon atoms. For example, $C_{6-12}$aryl can be phenyl, biphenyl or naphthyl, preferably phenyl. "Arylene" means a divalent radical derived from an aryl group. For example, arylene as used in this application can be phenylene, biphenylene or naphthylene, preferably phenylene, more preferably 1,4-phenylene.

"Bicycloaryl" means a bicyclic ring assembly containing the number of ring carbon atoms indicated, wherein the rings are linked by a single bond or fused and at least one of the rings comprising the assembly is aromatic. For example bicycloaryl includes naphthyl, biphenyl, and the like. "Tricycloaryl" means a tri-cyclic ring assembly containing the number of ring carbon atoms indicated, wherein the rings are fused and at least one of the rings comprising the assembly is aromatic. For example, tricycloaryl includes anthracenyl and the like. "Bicycloarylene" is a divalent radical derived from a bicycloaryl group. "Heterotricycloaryl" means tricycloaryl as defined in this application provided that one or more carbon atoms is replaced by a heteroatom moiety selected from —N═, —NR—, —O—, —S—, —S(O)— and —S(O)$_2$— (wherein R of —NR— is hydrogen or $C_{1-4}$alkyl). "Heterotricycloarylene" is a divalent radical derived from a heterotricycloaryl group and includes, for example, 5,7-dihydro-oxazolo[4,5-f]isoindol-6-ylene. "Heterobicycloaryl" means bicycloaryl as defined in this application provided that one or more carbon atoms is replaced by a heteroatom moiety selected from —N═, —NR—, —O—, —S—, —S(O)— and —S(O)$_2$— (wherein R of —NR— is hydrogen or $C_{1-4}$alkyl). For example, $C_{8-10}$heterobicycloarylene, as used to describe Y of Formula I, includes benzooxazol-2-yl, benzothiazol-2-yl, and the like.

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl.

"Heteroaryl" means aryl, as defined in this application, provided that one or more of the ring carbon atoms indicated are replaced by a hetero atom moiety selected from N, O or S, and each ring is comprised of 5 to 6 ring atoms, unless otherwise stated. For example, heteroaryl as used in this application includes thiophenyl, pyridinyl, furanyl, isoxazolyl, benzoxazolyl or benzo[1,3]dioxolyl, preferably thiophenyl, furanyl or pyridinyl. "Heteroarylene" means heteroaryl, as defined in this application, provided that the ring assembly comprises a divalent radical.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group (s) present or generated in such projected reactions. Examples of suitable protecting groups may be found in Greene et al., "Protective Groups in Organic Synthesis", 2nd Ed., John Wiley & Sons, Inc., New York (1991). Preferred amino protecting groups include, but are not limited to, benzyloxycarbonyl (CBz), t-butyl-oxycarbonyl (Boc), T-butyldimethylsilyl (TBDMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzyl, 5-bromo-7- nitroindolinyl, and the like. Preferred hydroxy protecting groups include Fmoc, TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy- methyloxycarbonyl).

DETAILED DESCRIPTION OF THE INVENTION

The invention provides compounds that are useful for treating or preventing diseases or disorders that are mediated by PDF activity. In one embodiment, for compounds are of Formula I: n is 1 or 2; Z is selected from —$CH_2$—, —$CH_2CH_2$— and —S—; $R_1$ is selected from hydrogen, —XC(O)$NR_5OR_6$ and —$XNR_5COR_6$; wherein X is selected from a bond, $C_{1-6}$alkylene, $C_{2-6}$alkenylene and $C_{2-6}$alkynylene; wherein X can be optionally substituted with hydroxy; $R_5$ is selected from hydrogen, hydroxy and $C_{1-4}$alkyl; and $R_6$ is selected from hydrogen and $C_{1-4}$alkyl; $R_2$ is selected from hydrogen, $C_{1-12}$alkyl, $C_{2-12}$alkenyl, halo-substituted-$C_{1-12}$alkyl, —$XOR_5$, —$XOR_7$, —XC(O)$OR_5$, —XOC(O)$R_5$, —XC(O)$NR_5R_6$, —XC(O)$NR_5R_7$, —XC(O)$NR_5OR_6$, —$XR_7$, —$XCHR_7R_7$, —XC(O)$R_6$, —$XOXOR_6$, —$XOXOR_7$, —$XOXR_7$, —XC(O)$R_7$, —XC≡N, —XC(O)$NR_5XR_7$ and —XC(O)$NR_5XNR_5R_6$; wherein X, $R_5$ and $R_6$ are as described above and $R_7$ is selected from $C_{3-10}$cycloalkyl, $C_{5-8}$heterocycloalkyl, $C_{6-10}$aryl and $C_{5-8}$heteroaryl; wherein any cycloalkyl, heterocycloalkyl, aryl or heteroaryl of $R_7$ can be optionally substituted by one to three radicals selected from halo, $C_{1-4}$alkyl, $C_{1-4}$alkoxy, cyano and —XC(O)$OR_5$; wherein X and $R_5$ are as described above; and $R_3$ is selected from hydrogen and halo.

In another embodiment, $R_1$ is selected from hydrogen, —XC(O)$NR_5OR_6$ and —$XNR_5COR_6$; wherein X is selected from a bond, $C_{1-6}$alkylene, $C_{2-6}$alkenylene and $C_{2-6}$alkynylene; wherein X can be optionally substituted with hydroxy; $R_5$ is selected from hydrogen, hydroxy and $C_{1-4}$alkyl; and $R_6$ is selected from hydrogen and $C_{1-4}$alkyl; $R_2$ is selected from hydrogen, $C_{1-12}$alkyl, $C_{2-12}$alkenyl, halo-substituted-$C_{1-12}$alkyl, —$XOR_5$, —$XOR_7$, —XC(O)$OR_5$, —XOC(O)$R_5$, —XC(O)$NR_5R_6$, —XC(O)$NR_5R_7$, —XC(O)$NR_5OR_6$, —$XR_7$, —$XCHR_7R_7$, —XC(O)$R_6$, —$XOXOR_6$, —$XOXOR_7$, —$XOXR_7$, —XC(O)$R_7$, —XC≡N, —XC(O)$NR_5XR_7$ and —XC(O)NR5$XNR_5R_6$; wherein X, $R_5$ and $R_6$ are as described above and $R_7$ is selected from $C_{3-10}$cycloalkyl, $C_{5-8}$heterocycloalkyl, $C_{6-10}$aryl and $C_{5-8}$heteroaryl; wherein any cycloalkyl, heterocycloalkyl, aryl or heteroaryl of $R_7$ can be optionally substituted by one to three radicals selected from halo, $C_{1-4}$alkyl, $C_{1-4}$alkoxy, cyano and —XC(O)$OR_5$; wherein X and $R_5$ are as described above; and $R_3$ is selected from hydrogen and halo.

In another embodiment, Z is —S—.

In a further embodiment, $R_1$ is selected from hydrogen, methoxy-carbamoyl-methyl, hydroxy-carbamoyl-methyl, hydroxy-carbamoyl-hydroxy-methyl, (formyl-hydroxy-amino)-methyl and (acetyl-hydroxy-amino)-methyl.

In a further embodiment, $R_2$ is selected from hydrogen, carbamoyl-methyl, cyano-methyl, methyl, cyclopropyl-methyl, benzyl, hydroxy-carbamoyl-methyl, 2-methoxy-ethyl, 3,3,3-trifluoro-propyl, 3-methyl-butyl, 4-methyl-pentyl, pentyl, cyclobutyl-methyl, 1-methyl-2-oxo-2-phenyl-ethyl, cyclohexyl-methyl, cyclohexyl-ethyl, 3,3-dimethyl-2-oxo-butyl, but-3-enyl, pyridin-2-yl-carbamoyl-methyl, (3,4-difluoro-phenylcarbamoyl)-methyl, (2,6-diethyl-phenylcarbamoyl)-methyl, [1-(4-fluoro-phenyl)-ethyl-carbamoyl]-methyl, 2-oxo-2-pyrrolidin-1-yl-ethyl, (2,5-difluoro-benzylcarbamoyl)-methyl, propyl-carbamoyl-methyl, (2-dimethylamino-ethylcarbamoyl)-methyl, butyl, phenethyl, formyl-hydroxy-amino, 1-carbamoyl-ethyl, 2-[1,3]dioxolan-2-yl-ethyl, tetrahydro-pyran-2-yl-methyl, 2-fluoro-benzyl, 4-fluoro-benzyl, 2,4-difluoro-benzyl, 2-cyano-benzyl, 3-cyano-benzyl, 4-cyano-benzyl, 3-methoxy-benzyl, 2-(4-cyano-phenyl)-2-oxo-ethyl, carboxy-methyl, 2-(4-carboxy-methyl-ester-phenyl)-2-oxo-ethyl, pyridin-3-yl-carbamoyl-methyl, 3,7-dimethyl-octyl, 2-oxo-butyl, 2-(2-methoxy-ethoxy)-ethyl, 3,3-diphenyl-propyl, ethyl, 2-ethyl-butyl, 3-fluoro-propyl, 3-benzyloxy-propyl, 4-phenoxy-butyl, 2-(3-methoxy-phenyl)-2-oxo-ethyl, 2-(4-methoxy-phenyl)-2-oxo-ethyl, 4-carboxy-benzyl, 2-(1,3-dioxo-1,3-dihydro-isoindol-2-yl)-ethyl, nonyl, 3-methoxy-carbonyl-propyl, 4-cyano-butyl, 3-methyl-but-2-enyl, phenyl-propyl, ethoxy-ethyl, 4-methyl-pent-3-enyl, phenoxy-ethyl, 4-methoxycarbonyl-butyl, 4-acetoxy-butyl, 4-propionyloxy-butyl and hexyl.

Preferred compounds of the invention are shown in table 1, infra.

The invention provides forms of the compound that have the hydroxyl or amine group present in a protected form; these function as prodrugs. Prodrugs are compounds that are converted into an active drug form after administration, through one or more chemical or biochemical transformations. The antibacterial potency of compounds that are potent inhibitors of the PDF enzyme in vitro, but penetrate the cell wall poorly, can be improved by their use in the form of a prodrug that is converted to the parent molecule after passing through the cell wall. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes.

Compounds of Formula I can exist in free form or in salt form, e.g. addition salts with inorganic or organic acids. Where hydroxyl groups are present, these groups can also be present in salt form, e.g. an ammonium salt or salts with metals such as lithium, sodium, potassium, calcium, zinc or magnesium, or a mixture thereof. Compounds of Formula I and their salts in hydrate or solvate form are also part of the invention.

When the compounds of Formula I have asymmetric centers in the molecule, various optical isomers are obtained. The present invention also encompasses enantiomers, racemates, diastereoisomers and mixtures thereof. Moreover, when the compounds of Formula I include geometric isomers, the present invention embraces cis-compounds, trans-compounds and mixtures thereof. Similar considerations apply in relation to starting materials exhibiting asymmetric carbon atoms or unsaturated bonds as mentioned above.

Methods for Preparing Antibacterial Compounds

The present invention also includes processes for the preparation of antibacterial compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following reaction scheme 1:

Reaction Scheme I

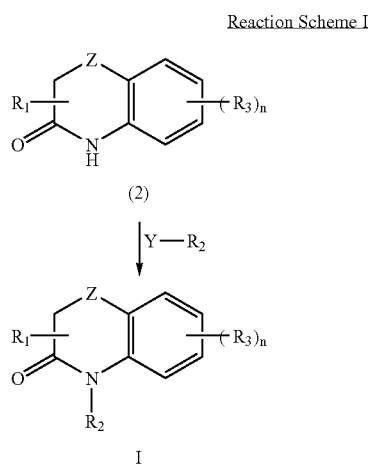

in which n, Z, $R_1$, $R_2$ and $R_3$ are as defined for Formula I, above. Y is a halogen, or the like. The reaction can proceed in the presence of a suitable base (e.g., NaH, LDA or the like) in a suitable solvent (e.g., DMF, THF, DMSO or the like) at a temperature of about 25° C. and can take up to 12 hours to complete.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from the their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(b) (a) reaction scheme 1; or (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples provide detailed descriptions of the preparation of representative compounds and are offered to illustrate, but not to limit the present invention.

Example 1

2-(2-Hydroxycarbamoylmethyl-3-oxo-2,3-dihydro-benzo[1,4]thiazin-4-yl)-propionamide

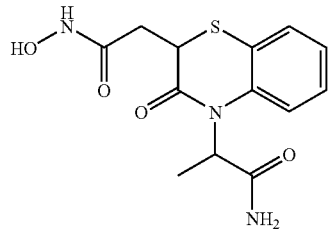

To a solution of (3-oxo-3,4-dihydro-2H-benzo[1,4]thiazin-2-yl)-acetic acid ethyl ester (0.59 mmol) in 1 mL of anhydrous DMF is added NaH (60% in mineral oil) (0.77 mmol) and the mixture is stirred at room temperature for 20 minutes. 2-Bromo propionamide is then added and the reaction is stirred at room temperature for 12 hours. The solvent is evaporated and the crude [4-(1-carbamoyl-ethyl)-3-oxo-3,4-dihydro-2H-benzo[1,4]thiazin-2-yl]-acetic acid ethyl ester is used in the next step without further purification.

The [4-(1-carbamoyl-ethyl)-3-oxo-3,4-dihydro-2H-benzo[1,4]thiazin-2-yl]-acetic acid ethyl ester obtained in the previous step is dissolved in 500 μL of MeOH and 500 μL of DMF and treated with 400 μL of LiOH (3M). The reaction is stirred at room temperature for 12 hours and then the solvent is evaporated. The resulting mixture is diluted with EtOAc and washed with HCl (1M). The organic layer is dried over $Na_2SO_4$, filtered and the solvent evaporated. The crude [4-(1-carbamoyl-ethyl)-3-oxo-3,4-dihydro-2H-benzo[1,4]thiazin-2-yl]-acetic acid is used in the next step without further purification.

The crude [4-(1-carbamoyl-ethyl)-3-oxo-3,4-dihydro-2H-benzo[1,4]thiazin-2-yl]-acetic acid is dissolved in 1 mL of anhydrous THF and EtCOCl (0.71 mmol) is added at 0° C. followed by N-methylmorpholine (0.76 mmol). The reaction mixture is stirred at 0° C. for 10 minutes. Freshly prepared $NH_2OH$ (1M in MeOH) (0.88 mmol) is added and the reaction stirred at room temperature for 15 minutes. After evaporation of the solvent the final 2-(2-hydroxycarbamoylmethyl-3-oxo-2,3-dihydro-benzo[1,4]thiazin-4-yl)-propionamide is obtained by preparative LC/MS (in the absence of TFA) using 1 to 99% ACN as gradient. $^1$H NMR (400 MHz, MeOD): δ 7.28 (m, 1H), 7.18 (m, 1H), 7.04 (m, 1H), 6.96 (m, 1H), 5.26 (m, 1H), 3.73 (m, 1H), 2.5 (m, 1H), 2.19 (m, 1H), 1.26 (m, 3H). MS: (ES$^+$): 332.2 [M+23].

Example 2

2-(2-Hydroxycarbamoylmethyl-3-oxo-2,3-dihydro-benzo[1,4]thiazin-4-yl)-N-(pyridin-2-yl)acetamide

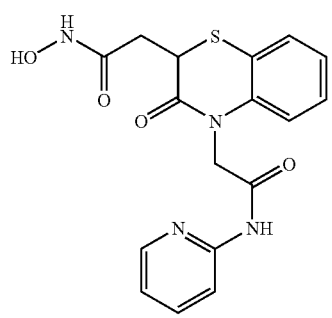

To a solution of LDA (2M) in THF (3.26 mmol) in 2 mL of anhydrous THF at 0° C. and under nitrogen, a solution of (3-oxo-3,4-dihydro-2H-benzo[1,4]thiazin-2-yl)-acetic acid ethyl ester (1.62 mmol) in 4 mL of dry THF is added dropwise. The temperature of the reaction mixture is held at room temperature for 2 hours and then dropped to −78° C. A solution of 2-bromo acetic acid (1.64 mmol) in 2 mL of anhydrous THF is added and the temperature of the reaction is slowly let to rise to room temperature. HCl (1M) is added to reach pH=1. Ethyl ether is added and the phases are separated. The organic phase is dried on $Na_2SO_4$, the drying agent is filtered and the solvent evaporated. The crude product is purified by automated column chromatography (hexane/EtOAc) to give the product ethyl 2-(3,4-dihydro-4-(carboxymetyl)-3-oxo-2H-benzo[b][1,4]thiazin-2-yl)acetate. Yield: 50%. $^1$H NMR (400 MHz, CDCl$_3$): δ 9.07 (bs, 1H), 7.38 (d, J=7.6 Hz, 1H), 7.27 (t, J=7.6 Hz, 1H), 7.07 (t, J=7.6 Hz, 1H), 6.93 (d, J=7.6 Hz, 1H), 4.69 (dd, 2H), 4.18 (dd, 2H), 3.99 (t, J=6.4 Hz, 1H), 3.04 (dd, J$_1$=6.4 Hz, J$_2$=16.8 Hz, 1H), 2.58 (dd, 1H), 1.26 (m, 3H).

To a solution of 2-(3,4-dihydro-4-(carboxymetyl)-3-oxo-2H-benzo[b][1,4]thiazin-2-yl)acetate (0.35 mmol) in 1 mL of anhydrous DMF is added 2-amino pyridine (0.42 mmol), DIEA (0.42 mmol) and HATU (0.42 mmol). The reaction mixture is then stirred for 4 hours. After the evaporation of the solvent the 2-(2-carboethoxymethyl-3-oxo-2,3-dihydro-benzo[1,4]thiazin-4-yl)-N-(pyridin-2-yl)acetamide is obtained by automated column chromatography (hexane/EtOAc). Yield: 40%.

The 2-(2-carboethoxymethyl-3-oxo-2,3-dihydro-benzo[1,4]thiazin-4-yl)-N-(pyridin-2-yl)acetamide obtained in the previous step is dissolved in 1 mL of MeOH and treated with 430 μL of LiOH (3M). The reaction is stirred at room temperature for 12 hours and then the solvent is evaporated. The resulting mixture is diluted with EtOAc and washed with HCl (1M). The organic layer is dried over $Na_2SO_4$, filtered and the solvent evaporated.

The crude 2-(2-carboxymethyl-3-oxo-2,3-dihydro-benzo[1,4]thiazin-4-yl)-N-(pyridin-2-yl)acetamide is dissolved in 0.5 mL of anhydrous ethyl ether and EtCOCl (0.043 mmol) is added at 0° C. followed by N-methylmorpholine (0.044 mmol). The reaction mixture is stirred at 0° C. for 10 minutes. Freshly prepared $NH_2OH$ (1M in MeOH) (0.054 mmol) is added and the reaction stirred at room temperature for 15 minutes. The final 2-(2-hydroxycarbamoylmethyl-3-oxo-2,3-dihydro-benzo[1,4]thiazin-4-yl)-N-(pyridin-2-yl)acetamide is obtained by preparative LC/MS (in the absence of TFA) using 1 to 99% ACN as gradient. $^1$H NMR (400 MHz, MeOD) δ 8.23 (d, 1H, J=8.0 Hz), 7.90 (t, 1H, J=8.0 Hz), 7.80 (d, 1H, J=8.0 Hz), 7.32 (d, 1H, J=9.0 Hz), 7.20 (m, 2H), 7.05 (d, 1H, J=9.0 Hz), 7.01 (t, 1H, J=8.0 Hz), 4.77 (s, 2H), 3.91 dd, 1H, J=6.6 Hz, J=8.8 Hz), 2.65 (dd, 1H, J=6.6 Hz, J=14.4 Hz), 2.28 (dd, 1H, J=8.8 Hz, J=14.4 Hz).MS: (ES+): 373.20 [M+1].

Example 3

2-(8-Bromo-3-oxo-3,4-dihydro-2H-benzo[1,4]thiazin-2-yl)-N-hydroxy-acetamide

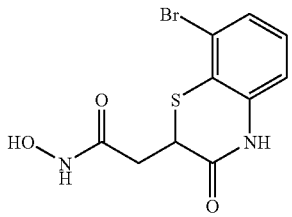

A solution of 2-chloro-1,3-dinitro-benzene (10 mmol) in 30 mL of DMF is cooled down to 0° C. 2-Mercapto-succinic acid bis-(3-methyl-butyl) ester (11 mmol) is added as one portion. After the addition, $Et_3N$ (12 mmol) is added dropwise into the mixture while keeping the temperature at 0° C. After stirring at 0° C. for 2 hours, the mixture is poured into water (300 mL) and is extracted with EtOAc (3×50 mL). The organic layers are combined and washed with brined and dried over $MgSO_4$. After filtering off the drying agent, the filtrate is concentrated and purified by flash column chromatography (silica gel, 0~25% EtOAc/hexane) to provide the desired product 2-(2,6-dinitro-phenylsulfanyl)-succinic acid bis-(3-methyl-butyl) ester as dark red oil. Yield: 59%. MS: ($ES^+$): 457 [M+1].

Iron powder (108.7 mmol) is added to a solution of 2-(2,6-dinitro-phenylsulfanyl)-succinic acid bis-(3-methyl-butyl) ester (4.35mmol) in 40 mL EtOH, followed by the addition of 8 mL of water and 4 mL of HCl (1M). The mixture is heated to 90° C. and stirred for 3 hours. After filtering off the iron, the mixture is cooled down to room temperature and concentrated. The residue is purified by flash column chromatography. (silica gel, 0-30% EtOAc/hexane) to provide the desired product (8-amino-3-oxo-3,4-dihydro-2H-benzo[1,4]thiazin-2-yl)-acetic acid 3-methyl-butyl ester as off white solid. Yield: 80%. MS: ($ES^+$): 309[M+1].

To a solution of (8-amino-3-oxo-3,4-dihydro-2H-benzo[1,4]thiazin-2-yl)-acetic acid 3-methyl-butyl ester (0.49 mmol) in 3 mL of acetonitrile, tert-butylnitrite is added (0.73 mmol) followed by $CuBr_2$ (0.59 mmol) at 0° C. After the mixture is stirred at 0° C. for 30 minutes, it is poured into 10 mL of HCl (1M) solution and extracted with EtOAc (20 mL). The organic layer is collected and washed with brine and dried over $MgSO_4$. After filtering off the drying agent, the filtrate is concentrated and purified by flash column chromatography (silica gel, 0~15% EtOAc/hexane) to provide the desired product (8-bromo-3-oxo-3,4-dihydro-2H-benzo[1,4]thiazin-2-yl)-acetic acid 3-methyl-butyl ester as white solid. Yield: 24%. MS: ($ES^+$): 372 [M+1].

To a solution of (8-bromo-3-oxo-3,4-dihydro-2H-benzo[1,4]thiazin-2-yl)-acetic acid 3-methyl-butyl ester (0.12 mmol) obtained from the previous reaction in 2 mL of EtOH is added NaOH (1N) (0.24 mmol). After the mixture is stirred at room temperature for 2 hours, 0.3 mL of HCl (1M) is added. The mixture is then extracted with EtOAc (3×5 mL). The organic layers are combined, concentrated and redissolved in 2 mL of anhydrous $Et_2O$. Following a similar procedure as described in Example 1, the 8-bromo-3-oxo-3,4-dihydro-2H-benzo[1,4]thiazin-2-yl)-acetic acid is converted to the title compound 2-(8-bromo-3-oxo-3,4-dihydro-2H-benzo[1,4]thiazin-2-yl)-N-hydroxy-acetamide and purified by preparative thin layer chromatography. $^1$H NMR (400 MHz, MeOD) δ 7.18 (d, 1H, J=8.0 Hz), 6.70 (t, 1H, J=8.0 Hz), 6.85 (d, 1H, J=8.0 Hz), 3.88 (dd, 1H, J=9.0 Hz, J=5.6 Hz), 2.66 (dd, 1H, J=5.6Hz, J=14.9 Hz), 2.25 (dd, 1H, J=9.0 Hz, J=14.9 Hz). MS: ($ES^+$): 317.10 [M+1].

Example 4

2,N-Dihydroxy-2-(3-oxo-3,4-dihydro-2H-benzo[1,4]thiazin-2-yl)-acetamide

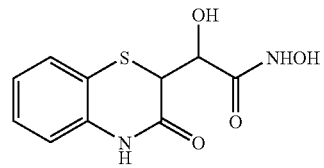

To a solution of 4H-benzo[1,4]thiazin-3-one (6.06 mmol) in 30 mL of anhydrous THF at −78° C. is added freshly prepared LDA (13.9 mmol) dropwise. After the mixture is stirred at −78° C. for 30 minutes, it is warmed up to 0° C for 30 minutes and cooled down to −78° C. again. The resulting mixture is then slowly transferred using a double-ended needle into a solution of ethyl glyoxalate (18.3 mmol, 50% in toluene) in 10 mL of anhydrous THF kept at −78° C. After the addition, the mixture is allowed to slowly warm up to 0° C. and to stir for 3 hours. 2 mL of a mixture of EtOH and water (1:1) is added to quench the reaction and the mixture is poured into a saturated aqueous solution of $NH_4Cl$ (50 mL). After the extraction with EtOAc (3×40 mL), the organic layers are combined and washed with brine and dried over $MgSO_4$. After filtering off the drying agent, the solution is concentrated and purified by flash column chromatography (silica gel, 0 2% EtOH/$CH_2Cl_2$) to provide the desired product hydroxy-(3-oxo-3,4-dihydro-2H-benzo[1,4]thiazin-2-yl)-acetic acid ethyl ester as a white solid. Yield: 32%. MS: (ES+): 268 [M+1].

To a solution of hydroxy-(3-oxo-3,4-dihydro-2H-benzo[1,4]thiazin-2-yl)-acetic acid ethyl ester (1.12mmol) in 5 mL of EtOH is added NaOH (1N) (2.24 mmol) and the mixture is stirred at room temperature for 1 hour. Water (20 ml) is added into the mixture followed by extraction (EtOAc, 3×10 mL). The aqueous layer is then treated with HCl (1N) (2.5 mL) and extracted with EtOAc (3×30 mL). The combined extracts are washed with brine and dried over $MgSO_4$. After filtering off the drying agent, the solution is concentrated to provide the crude product hydroxy-(3-oxo-3,4-dihydro-2H-benzo[1,4]thiazin-2-yl)-acetic acid as a off white solid. Yield: 76%. MS: ($ES^+$): 240 [M+1].

A mixture of hydroxy-(3-oxo-3,4-dihydro-2H-benzo[1,4]thiazin-2-yl)-acetic acid (0.13 mmol) and p-TSA (1 mg) in 1.5 mL of 2,2-dimethoxypropane is stirred at room temperature for 16 hours. Solvent is removed under vacuum and the residue is treated with a saturated aqueous solution of $NaHCO_3$ (2 mL). The resulted mixture is extracted with EtOAc (3×5 mL). The organic layers are combined and concentrated to provide the crude 2-(2,2-dimethyl-5-oxo-[1,3]dioxolan-4-yl)-4H-benzo[1,4]thiazin-3-one which is used directly for next step without further purification. Yield: 31%

The crude 2-(2,2-dimethyl-5-oxo-[1,3]dioxolan-4-yl)-4H-benzo[1,4]thiazin-3-one (0.036 mmol) is dissolved in 0.5 mL of THF and 0.5 mL of $NH_2OH$ (1N in MeOH) is added to the mixture. After the addition, the mixture is stirred at 60° C. for 3 hours. The solvent is then removed under vacuum and the residue is purified by preparative thin layer chromatography (silica gel, 10% MeOH/CH$_2$Cl$_2$) to provide the title compound 2,N-dihydroxy-2-(3-oxo-3,4-dihydro-2H-benzo[1,4]thiazin-2-yl)-acetamide. Yield: 70%. $^1$H NMR (400 MHz, MeOD) δ 7.30 (dd, 1H, J=1.29 Hz, J=8.0 Hz), 7.18, (dt, 1H, J=1.3 Hz, J=8.0 Hz), 7.01 (dt, 1H, J=1.3 Hz, J=8.0 Hz), 6.95 (dd, 1H, J=1.3 Hz, J=8.0 Hz), 4.74 (d, 1H, J=3.80), 3.97 (d, 1H, J=3.8). MS: (ES$^+$): 255.1[M+1].

Example 5

N-Hydroxy-N-(3-oxo-3,4-dihydro-2H-benzo[1,4]thiazin-2-ylmethyl)-formamide

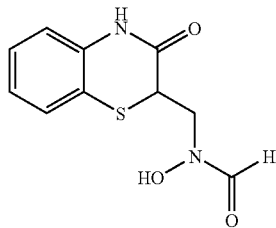

4H-Benzo[1,4]thiazin-3-one (165 mmol) is dissolved in 60 mL of CH$_2$Cl$_2$ and then sulfuryl chloride is added (135 mmol) slowly over a 30 minute period. The mixture is stirred for 12 hours and then the solvent is evaporated. The crude 2-chloro4H-benzo[1,4]thiazin-3-one is used in the next step without further purification.

2-Chloro-4H-benzo[1,4]thiazin-3-one (60.5 mmol) is dissolved in triethylphosphite (269 mmol) and the mixture is heated to 100° C. The color gradually changes from pale yellow to orange. After 2 hours the excess triethylphosphite is removed under vacuum and the product (3-oxo-3,4-dihydro-2H-benzo[1,4]thiazin-2-yl)-phosphonic acid diethyl ester is purified by column chromatography (hexane/EtOAc). Yield: 40%. $^1$H NMR (400 MHz, CDCl$_3$): δ 7.25 (m, 1H), 7.09 (m, 1H), 6.94 (m, 1H), 6.82 (m, 1H), 4.08 (m, 2H), 3.96 (m, 1H), 3.79 (m, 2H), 1.20 (t, 3H), 0.95 (t, 3H). MS: (ES$^+$): 302.2 [M+1].

(3-Oxo-3,4-dihydro-2H-benzo[1,4]thiazin-2-yl)-phosphonic acid diethyl ester (12.2 mmol) is dissolved in 40 mL of anhydrous MeOH and formaldehyde (37%) in water (12.2 mmol) is added to the orange solution. NaOMe (2N in MeOH) (12.2 mmol) is added and the reaction is cooled down to 0° C. The solid that precipitates is filtered to give 2-methylene-4H-benzo[1,4]thiazin-3-one. Yield: 72%. $^1$H NMR (400 MHz, CDCl$_3$): δ 9.03 (s, 1H), 7.06 (m, 2H), 6.94 (m, 1H), 6.81 (m, 1H), 6.80 (s, 1H), 5.62 (s, 1H). MS: (ES$^+$): 178.2 [M+1].

To a solution of 2-methylene-4H-benzo[1,4]thiazin-3-one (5.14 mmol) in 10 mL of anhydrous DMF, Et$_3$N (25.7 mmol) is added followed by O-benzylhydroxylamine hydrochloride (25.7 mmol). The mixture is stirred at 100° C. for 12 hours and then the solvent is evaporated. The crude is purified by column chromatography (hexane/EtOAc) to give 2-(benzyloxyamino-methyl)-4H-benzo[1,4]thiazin-3-one. Yield 58%. $^1$H NMR (400 MHz, CDCl$_3$): δ 8.51 (s, 1H), 7.13 (m, 9H), 6.1 (bs, 1H), 4.64 (s, 2H), 3.86 (m, 1H), 3.3 (m, 1H), 2.9 (m, 1H). MS: (ES$^+$): 301.2 [M+1].

To a solution of 2-(benzyloxyamino-methyl)-4H-benzo[1,4]thiazin-3-one (2.96 mmol) in 15 mL of formic acid at 0° C., acetic anhydride is added (15.1 mmol) and the reaction is stirred at room temperature overnight. The mixture is diluted with EtOAc and washed with water followed by brine and NaHCO$_3$. Purification by column chromatography (hexane/EtOAc) gives N-benzyloxy-N-(3-oxo-3,4-dihydro-2H-benzo[1,4]thiazin-2-ylmethyl)-formamide. Yield: 81%. MS: (ES$^+$): 329.2 [M+1].

To a solution of N-benzyloxy-N-(3-oxo-3,4-dihydro-2H-benzo[1,4]thiazin-2-ylmethyl)-formamide (0.17 mmol) in EtOH (12 mL) is added Pd/C (10%) (88.5 mg) followed by cyclohexadiene (1.8 mL). The reaction mixture is stirred at room temperature for 12 hours and the final product N-hydroxy-N-(3-oxo-3,4-dihydro-2H-benzo[1,4]thiazin-2-ylmethyl)-formamide is obtained by preparative LC/MS using 1 to 99% ACN as gradient. $^1$H NMR (400 MHz, MeOD): δ 8.48 (s, 0.4H), 7.97 (s, 0.6H), 7.49 (m, 2H), 7.19 (m, 2H), 4.03 (m, 2H), 3.5 (dd, 1H). MS: (ES$^+$): 239.1[M+1].

Example 6

2-{2-[(Benzaloxy-formyl-amino)-methyl]-3-oxo-2,3-dihydro-benzo[1,4]thiazin-4-yl}-N-propyl-acetamide

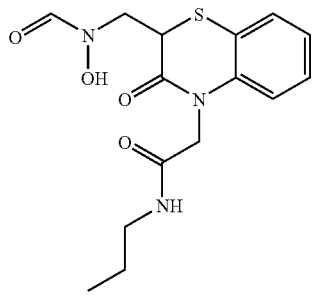

To a solution of N-benzyloxy-N-(3-oxo-3,4-dihydro-2H-benzo[1,4]thiazin-2-ylmethyl)-formamide (2.4mmol), synthesized as described in example 5, in anhydrous DMF is added NaH (60% in mineral oil) (3.36 mmol) and the mixture is stirred at room temperature for 30 minutes. Tert-butyl bromoacetate is then added and the reaction is stirred at room temperature overnight. The solvent is evaporated and the crude {2-[(benzyloxy-formyl-amino)-methyl]-3-oxo-2,3-dihydro-benzo [1,4]thiazin-4-yl}-acetic acid tert-butyl ester is used in the next step without further purification.

The {2-[(benzyloxy-formyl-amino)-methyl]-3-oxo-2,3-dihydro-benzo[1,4]thiazin-4-yl}-acetic acid tert-butyl ester obtained in the previous step is treated with TFA (2.4 mmol) in 12 mL of formic acid. The reaction is stirred at room temperature for 3 hours. The solvent is removed and the mixture is purified by column chromatography (hexane/EtOAc) yielding {2-[(benzyloxy-formyl-amino)-methyl]-3-oxo-2,3-dihydro-benzo[1,4]thiazin-4-yl}-acetic acid. Yield: 50%. MS: (ES$^+$): 359.2 [M+1].

To a solution of {2-[(benzyloxy-formyl-amino)-methyl]-3-oxo-2,3-dihydro-benzo[1,4]thiazin-4-yl}-acetic acid (0.13 mmol) in anhydrous DMF, propylamine (0.13 mmol) is added followed by DIEA (0.13 mmol) and HATU (0.13 mmol). The reaction mixture is stirred overnight and the desired product 2-{2-[(benzyloxy-formyl-amino)-methyl]-3-oxo-2,3-dihydro-benzo [1,4]thiazin-4-yl}-N-propyl-acetamide is obtained and used in the next step without further purification. MS: (ES$^+$): 428.2 [M+1].

To a solution of 2-{2-[(benzyloxy-formyl-amino)-methyl]-3-oxo-2,3-dihydro-benzo[1,4]thiazin-4-yl}-N-propyl-acetamide (0.13 mmol) in 9 ml of EtOH is added Pd/C (10%) (65.6 mg) followed by 1,4-cyclohexadiene (1.29 mL). The reaction mixture is stirred at room temperature for 12 hours and the final product 2-{2-[(formyl-hydroxy-amino)-methyl]-3-oxo-2,3-dihydro-benzo[1,4]thiazin-4-yl}-N-propylacetamide is obtained by preparative LC/MS using 1 to 99% ACN (in the absence of TFA) as gradient. MS: (ES+): 338.2 [M+1].

Example 7

2-(7-Chloro-3-oxo-2,3-dihydro-benzo[1,4]thiazin-4-yl)-N-hydroxy-acetamide

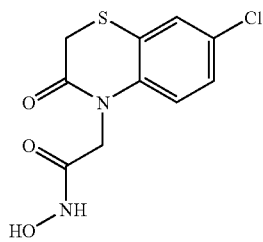

A solution of LDA (2M) (2 mmol) in THF/heptane/ethylbenzene is added dropwise to a solution of 7-chloro-4H-benzo[1,4]thiazin-3-one (1 mmol) in 2 mL of anhydrous THF kept at 0° C. and under nitrogen. The resulting solution is stirred at 0° C. for 30 minutes. The reaction mixture is cooled down to −78° C. and then a solution of bromoacetic acid (0.82 mmol) in 2 mL of anhydrous THF is added. The stirring is continued for 12 hours allowing the temperature to rise to room temperature. The resulting mixture is diluted with EtOAc and washed with HCl (1M). The organic layer is dried over Na$_2$SO$_4$, filtered and the solvent evaporated. The crude (7-chloro-3-oxo-2,3-dihydro-benzo[1,4]thiazin-4-yl)-acetic acid is used in the next step without further purification.

The (7-chloro-3-oxo-2,3-dihydro-benzo[1,4]thiazin-4-yl)-acetic acid obtained in the previous step is dissolved in 3 mL of Et$_2$O and EtCOCl (1.2 mmol) is added at 0° C. followed by N-methylmorpholine (1.3 mmol). The reaction mixture is stirred at 0° C. for 10 minutes. Freshly prepared NH$_2$OH (1M in MeOH) (1.5 mmol) is added and the reaction stirred at room temperature for 15 minutes. The final 2-(7-chloro-3-oxo-2,3-dihydro-benzo[1,4]thiazin-4-yl)-N-hydroxy-acetamide is obtained by preparative LC/MS (in the absence of TFA) using 1 to 99% ACN as gradient. $^1$H NMR (400 MHz, MeOD): δ 8.95 (s, 1H), 7.5 (s, 1H), 7.3 (d, 1H), 7.05 (d, 1H), 4.35 (s, 2H), 3.6 (s, 2H). MS: (ES+): 295.05 [M+23].

Example 8

2-(3,4-dihydro-3-oxo-2H-benzo[b][1,4]thiazin-2-yl)-N-methoxyacetamide

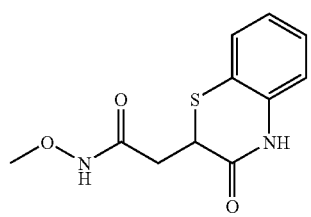

To a solution of (3-oxo-3,4-dihydro-2H-benzo[1,4]thiazin-2-yl)-acetic acid (0.21 mmol) in 1 mL of MeOH, K$_2$CO$_3$ (0.25 mmol) is added followed by MeI (0.25 mmol). The reaction mixture is stirred at room temperature for 12 hours and the final product 2-(3,4-dihydro-3-oxo-2H-benzo[b][1,4]thiazin-2-yl)-N-methoxyacetamide is obtained by preparative LC/MS using 10 to 30% ACN as gradient. MS: (ES+): 270.05 [M+23].

Example 9

N-Hydroxy-2-(2-oxo-1,2,3,4-tetrahydro-quinolin-3-yl)-acetamide

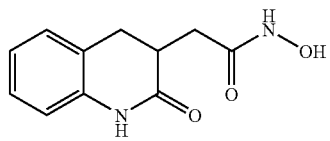

To a solution of 3,4-dihydro-1H-quinolin-2-one (27 mmol) in 250 mL of anhydrous DMF is added NaH (60% in mineral oil) (30 mmol) and the mixture is stirred at room temperature for 30 minutes. 4-Methoxybenzyl chloride (30 mmol) is then added and the reaction mixture is stirred at room temperature for 2 hours. The solvent is evaporated. The residue is dissolved in 100 mL of water and extracted with CH$_2$Cl$_2$ three times. The combined organic layers are dried over MgSO$_4$, filtered, and evaporated to give the crude 1-(4-methoxy-benzyl)-3,4-dihydro-1H-quinolin-2-one, which is used in the next step without further purification. Yield: 95%.

The 1-(4-methoxy-benzyl)-3,4-dihydro-1H-quinolin-2-one (7.86 mmol) obtained in the previous step is dissolved in 10 mL of anhydrous THF. A solution of freshly prepared LDA (9.43 mmol) in 3.5 mL of anhydrous THF is added dropwise at −78° C. The reaction mixture is stirred at −78° C. for 10 minutes, warmed up to 0° C. for 15 minutes, and then cooled down to −78° C. again before it is transferred dropwise through a double-ended needle to a solution of tert-butyl bromoacetate (10.2 mmol) in 5 mL of anhydrous THF. The resultant solution is stirred at —78° C. for 1 hour before it is allowed to warm up to 0° C. within another hour and then quenched with MeOH. After removal of the solvent, the residue is purified by silica gel chromatography (hexane/EtOAc) to give [1-(4-methoxy-benzyl)-2-oxo-1,2,3,4-tetrahydro-quinolin-3-yl]-acetic acid tert-butyl ester as a light yellow oil. Yield: 53%. $^1$H NMR (400 MHz, CDCl$_3$): δ 7.13 (m, 4H), 6.96 (t, 1H), 6.90 (d, 1H), 6.83 (d, 2H), 5.25 (d, 1H), 4.95 (d, 1H), 3.76 (s, 3H), 3.13 (m, 1H), 3.00-2.85 (m, 3H), 2.41 (dd, 1H), 1.48 (s, 9H). MS: (ES+): 404.2 [M+23].

The [1-(4-methoxy-benzyl)-2-oxo-1,2,3,4-tetrahydro-quinolin-3-yl]-acetic acid tert-butyl ester (3.35 mmol) obtained in the previous step is dissolved in 7 mL of TFA and heated to reflux for 1.5 hours. After removal of the excess TFA under reduced pressure, acid-base extraction gives the crude (2-oxo-1,2,3,4-tetrahydro-quinolin-3-yl)-acetic acid as a yellow solid. Yield: 93%.

Following a similar procedure described in example 1, the (2-oxo-1,2,3,4-tetrahydro-quinolin-3-yl)-acetic acid obtained in the previous step is converted into the final N-hydroxy-2-(2-oxo-1,2,3,4-tetrahydro-quinolin-3-yl)-acetamide. MS: (ES+): 243.2 [M+23].

Example 10

N-Hydroxy-2-[1-(3-methyl-butyl)-2-oxo-1,2,3,4-tetrahydro-quinolin-3-yl]-acetamide

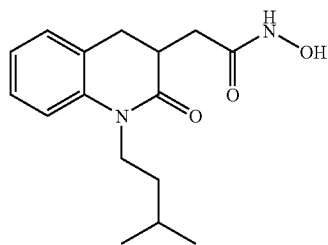

(2-Oxo-1,2,3,4-tetrahydro-quinolin-3-yl)-acetic acid (2.73 mmol), EDCl (3.27 mmol) and DIEA (3.27 mmol) are dissolved in 10 mL MeOH. About 2 mL of CH$_2$Cl$_2$ is also added to help dissolving the solid. The reaction mixture is stirred at room temperature for 2 hours before removal of the solvent under reduced pressure. The residue is purified by silica gel chromatography (hexane/EtOAc) to give (2-oxo-1,2,3,4-tetrahydro-quinolin-3-yl)-acetic acid methyl ester as a white solid. Yield: 60%. $^1$H NMR (400 MHz, CDCl$_3$): δ 7.88 (br, 1H), 7.18 (m, 2H), 7.00 (td, 1H), 6.75 (d, 1H), 3.73 (s, 3H), 3.13-2.98 (m, 3H), 2.89 (m, 1H), 2.51 (dd, 1H). MS: (ES$^+$): 220.2 [M+1].

Following a similar N-alkylation procedure described in example 9, the (2-oxo-1,2,3,4-tetrahydro-quinolin-3-yl)-acetic acid methyl ester (0.068 mmol) obtained in the previous step is alkylated with 1-bromo-3-methylbutane to give the crude [1-(3-methyl-butyl)-2-oxo-1,2,3,4-tetrahydro-quinolin-3-yl]-acetic acid methyl ester, which is used in the next step without further purification.

The crude [1-(3-methyl-butyl)-2-oxo-1,2,3,4-tetrahydro-quinolin-3-yl]-acetic acid methyl ester obtained in the previous step is dissolved in 0.5 mL of anhydrous THF. Freshly prepared NH$_2$OH (0.77 M in MeOH) (0.44 mL) (also containing 0.77M NaOH) is then added and the mixture is stirred at room temperature for 12 hours. The final product N-hydroxy-2-[1-(3-methyl-butyl)-2-oxo-1,2,3,4-tetrahydro-quinolin-3-yl]-acetamide is obtained by preparative LC/MS using 1 to 99% ACN as gradient. $^1$H NMR (400 MHz, MeOD): δ 7.29 (t, 1H), 7.20 (d, 1H), 7.11 (d, 1H), 7.04 (t, 1H), 3.97 (m, 2H), 3.02-2.89 (m, 2H), 2.77-2.65 (m, 2H), 2.17 (dd, 1H), 1.65 (m, 1H), 1.50 (m, 2H), 0.97 (2d, 6H). MS: (ES$^+$): 291.3 [M+1].

Example 11

N-Hydroxy-2-[2-oxo-1-(pyridin-2-ylcarbamoylmethyl)-1,2,3,4-tetrahydro-quinolin-3-yl]-acetamide

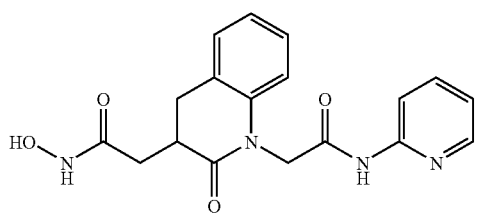

Following a similar N-alkylation procedure described in example 6, the (2-oxo-1,2,3,4-tetrahydro-quinolin-3-yl)-acetic acid methyl ester (0.99 mmol) is alkylated with tert-butyl bromoacetate to give (1-tert-butoxycarbonylmethyl-2-oxo-1,2,3,4-tetrahydro-quinolin-3-yl)-acetic acid methyl ester as a colorless oil, after purification by silica gel chromatography (hexane/EtOAc). Yield: 89%. MS: (ES$^+$): 356.2 [M+23].

The (1-tert-butoxycarbonylmethyl-2-oxo-1,2,3,4-tetrahydro-quinolin-3-yl)-acetic acid methyl ester (0.30 mmol) obtained in the previous step is dissolved in 1 mL of CH$_2$Cl$_2$/TFA (1:1). The reaction mixture is stirred at room temperature overnight before the solvent is removed under reduced pressure. The crude (3-methoxycarbonylmethyl-2-oxo-3,4-dihydro-2H-quinolin-1-yl)-acetic acid is used in the next step without further purification. Yield: 100%.

A solution of (3-methoxycarbonylmethyl-2-oxo-3,4-dihydro-2H-quinolin-1-yl)-acetic acid (0.072 mmol) obtained in the previous step, EDCl (0.087 mmol), 2-aminopyridine (0.087 mmol) and DIEA (0.087 mmol) in 0.5 mL of DCM is stirred at room temperature for overnight. After removal of the solvent, the crude [2-oxo-1-(pyridin-2-ylcarbamoylmethyl)-1,2,3,4-tetrahydro-quinolin-3-yl]-acetic acid methyl ester is used in the next step without further purification.

Following a similar procedure described in example 10, the crude [2-oxo-1-(pyridin-2-ylcarbamoylmethyl)-1,2,3,4-tetrahydro-quinolin-3-yl]-acetic acid methyl ester obtained in the previous step is converted to the final product N-hydroxy-2-[2-oxo-1-(pyridin-2-ylcarbamoylmethyl)-1,2,3,4-tetrahydro-quinolin-3-yl]-acetamide, which is purified by preparative LC/MS using 1 to 99% ACN as gradient. $^1$H NMR (400 MHz, MeOD): δ 8.30 (dd, 1H), 8.04 (d, 1H), 7.76 (td, 1H), 7.24 (m, 2H), 7.12 (dd, 1H), 7.05 (t, 1H), 6.99 (d, 1H), 4.91 (d, 1H), 4.76 (d, 1H), 3.13 (m, 1H), 3.03 (dd, 1H), 2.90 (dd, 1H), 2.73 (dd, 1H), 2.25 (dd, 1H). MS: (ES$^+$): 355.2 [M+1].

Example 12

N-Hydroxy-2-(2-oxo-2,3,4,5-tetrahydro-1H-benzo[b]azepin-3-yl)-acetamide

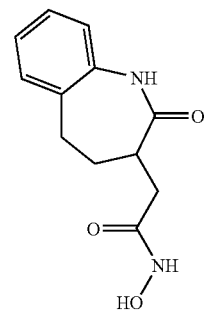

NaH (60% in mineral oil) (1.86 mmol) is added to a solution a 1,3,4,5-tetrahydro-benzo[b]azepin-2-one (1.55 mmol) in 5 mL of DMF at 0° C., After stirring at 0° C. for 15 minutes, the mixture is allowed to warm up to room temperature. p-Methoxybenzyl chloride (1.94 mmol) is added to the mixture. After stirring at room temperature for 16 hours, the mixture is poured into 50 mL of water and extracted with EtOAc (3×25 mL). The organic layer are combined, washed with brine and dried over MgSO$_4$. After removing the solvent under reduced pressure, the residue is purified by flash column chromatography (silica gel) to provide the desired product 1-(4-ethoxy-benzyl)-1,3,4,5-tetrahydro-benzo[b]azepin-2-one as white solid. Yield: 90%. MS: (ES+): 282.1 [M+1].

A solution of 1-(4-methoxy-benzyl)-1,3,4,5-tetrahydro-benzo[b]azepin-2-one (0.71 mmol) in 2 mL of anhydrous THF is cooled down to −78° C. and freshly prepared LDA (0.85 mmol) is slowly added to the mixture. After the addition, the mixture is allowed to warm up to 0° C., then stirred for 30 minutes and cooled down again to −78° C. Tert-butyl bromoacetate (1.0 mmol) is added. The mixture is stirred at −78° C. for 1 hour and then allowed to warm up to 0° C. To quench the reaction, 1 mL of a mixture of EtOH and water (1:1) is added to the mixture at 0° C. and the mixture is allowed to warm up to room temperature. Water (20 mL) is added followed by extraction (EtOAc, 3×15 mL). The combined organic layers are washed with brine and dried over MgSO$_4$. Solvent is removed under vacuum and the residue is purified by flash column chromatography (silica gel, 0-25% EtOAc/hexane) to provide the desired product [1-(4-methoxy-benzyl)-2-oxo-2,3,4,5-tetrahydro-1H-benzo[b]azepin-3-yl]-acetic acid tert-butyl ester as white solid. Yield: 30%. $^1$H NMR (400 MHz, CDCl$_3$): δ 7.24 (m, 2H), 7.13 (m, 4H), 6.75 (d, 2H), 5.10 (d, 1H), 4.80 (d, 1H), 2.86(m, 2H), 2.38-2.50(m, 2H), 2.17(q, 1H), 1.80-2.05(m, 2H), 1.40(s, 9H). MS: (ES+): 396 [M+1].

[1-(4-Methoxy-benzyl)-2-oxo-2,3,4,5-tetrahydro-1H-benzo[b]azepin-3-yl]-acetic acid tert-butyl ester (0.19 mmol) is dissolved in 1.5 mL of TFA and heated to 100° C. for 3 hours. The mixture is cooled down to room temperature and concentrated. The residue is treated with NaOH (1N) (1 mL) and extracted with EtOAc (3×1 mL). The aqueous layer is then neutralized to pH=2 with HCl (1M) and extracted with EtOAc (3×2 mL). The organic layers resulted from this extraction is concentrated to provide the crude (2-oxo-2,3,4,5-tetrahydro-1H-benzo[b]azepin-3-yl)-acetic acid. Yield: 72%.

The (2-oxo-2,3,4,5-tetrahydro-1H-benzo[b]azepin-3-yl)-acetic acid is treated with EtCOCl and freshly prepared NH$_2$OH by following a similar procedure described in example 1 to provide the title compound N-hydroxy-2-(2-oxo-2,3,4,5-tetrahydro-1H-benzo[b]azepin-3-yl)-acetamide which is purified by preparative LC/MS. $^1$H NMR (400 MHz, MeOD) δ 7.28 (m, 2H), 7.17(dt, 1H, J=1.2 Hz, J=8.0 Hz), 7.04 (dd, 1H, J=1.2 Hz, J 8.0 Hz), 2.90 (m, 2H), 2.72 (m, 1H), 2.55 (m, 1H), 2.28 (m, 1H), 2.15 (m, 1H), 1.97 (m, 1H). MS: (ES+): 235.3 [M+1].

Example 13

N-Hydroxy-N-(2-oxo-2,3,4,5-tetrahydro-1H-benzo[b]azepin-3-ylmethyl)-formamide

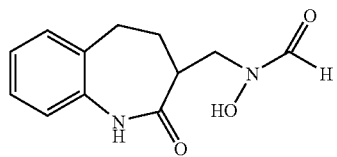

1-(4-Methoxy-benzyl)-1,3,4,5-tetrahydro-benzo[b]azepin-2-one (0.71 mmol) synthesized as described in example 12 is dissolved in 5 mL of anhydrous THF and cooled down to −78° C. A solution of freshly prepared LDA (0.85 mmol) is added to the mixture slowly. After stirring at the same temperature for 10 minutes, the mixture is allowed to warm up to 0° C. for 30 minutes and then cooled down to −78° C. again. Ethyl formate (3.55 mmol) is added dropwise to the reaction mixture. After the addition, the mixture is stirred at −78° C. for 10 minutes and then the temperature is risen to 0° C. for 1 hour. The reaction is quenched by addition of 1 mL of a mixture of water and EtOH (1:1), concentrated and dried under reduced pressure for 24 hours. The residue is redissolved in 4 mL of anhydrous THF, Na(AcO)$_3$BH (2.1 mmol) is added to the mixture and the resulting mixture is stirred at room temperature for 16 hours. The reaction mixture is poured into 20 mL of water and extracted with EtOAc (3×10 mL). The organic layers are combined, washed with brine and dried over MgSO$_4$. Solvent is removed under vacuum and the residue is purified by flash column chromatography (silica gel) to provide the desired product 3-hydroxymethyl-1-(4-methoxy-benzyl)-1,3,4,5-tetrahydro-benzo[b]azepin-2-one as white solid. Yield: 45%. MS: (ES+): 312 [M+1].

To a solution of 3-hydroxymethyl-1-(4-methoxy-benzyl)-1,3,4,5-tetrahydro-benzo[b]azepin-2-one (0.26 mmol) in 2 mL of anhydrous THF at 0° C. is added MsCl (0.39 mmol) and DIEA (0.47 mmol). After the addition, the mixture is allowed to warm up to room temperature and then stirred for 1 hour. The solvent is removed under vacuum and the residue is treated with water (5 mL) and extracted with EtOAc (3×5 mL). The combined organic layers are concentrated and the residue is purified by flash column chromatography (silica gel) to provide methanesulfonic acid 1-(4-methoxy-benzyl)-2-oxo-2,3,4,5-tetrahydro-1H-benzo[b]azepin-3-ylmethyl ester as white crystals. Yield: 90%. MS: (ES+): 390[M+1].

A mixture of methanesulfonic acid 1-(4-methoxy-benzyl)-2-oxo-2,3,4,5-tetrahydro-1H-benzo[b]azepin-3-ylmethyl ester (0.15 mmol) in 1 mL of TFA is heated at 80° C. for 3 hours. The solvent is removed under vacuum and the residue is treated with neat O-benzylhydroxylamine (0.2 mL) at 100° C. for 16 hours. The reaction mixture is cooled down and directly purified by flash column chromatography (silica gel, 1060% EtOAc/hexane) to provide the crude product 3-(benzyloxyamino-methyl)-1,3,4,5-tetrahydro-benzo[b]azepin-2-one as an oil which may still contain small amount of O-benzyl-hydroxylamine. The crude product is then added into a mixture of formic acid (1 mL) and acetic anhydride (0.2 mL) at 0° C. and the mixture is stirred at this temperature for 3 hours. The solvent is removed under reduced pressure and the residue is purified by preparative thin layer chromatography (silica gel, 50% EtOAc/hexane) to provide the desired product N-benzyloxy-N-(2-oxo-2,3,4,5-tetrahydro-1H-benzo[b]azepin-3-ylmethyl)-formamide as a white solid. Yield: 36%. MS: (ES+): 325 [M+1].

A mixture of N-benzyloxy-N-(2-oxo-2,3,4,5-tetrahydro-1H-benzo[b]azepin-3-ylmethyl)-formamide (0.052 mmol) and Pd/C (10%) (3 mg) in EtOH is degassed and filled with hydrogen. After the mixture is stirred at room temperature for 14 hours, Pd/C is removed by filtration. The filtrate is concentrated and purified by preparative thin layer chromatography (10% EtOH/CH$_2$Cl$_2$) to provide the title compound N-hydroxy-N-(2-oxo-2,3,4,5-tetrahydro-1H-benzo[b]azepin-3-ylmethyl)-formamide. Yield: 58%. $^1$H NMR (400 MHz, MeOD): δ 8.13 (s, 1H), 7.87 (s, 1H), 7.17 (m, 2H), 7.06 (t, 1H, J=8.0 Hz), 6.92 (d, 1H, J=8.0 Hz), 3.88 (dd, 1H, J=8.0 Hz, J=14.4 Hz), 3.24 (dd, 1H, J=4.8 Hz, J=14.4 Hz), 2.77 (m, 2H), 2.62 (m, 1H), 2.11 (m, 1H), 1.84 (m, 1H). MS: (ES+): 235.2 [M+1].

By repeating the procedure described in the above examples, using appropriate starting materials, the following compounds of Formula I are obtained as identified in Table 1.

TABLE 1

| Example | Compound | Physical Data ¹H NMR 400 MHz (DMSO-d₆) and/or MS (m/z) | Synthesis |
|---|---|---|---|
| 1 | (structure) | 332.2 [M + 23]; ¹H NMR (400 MHz, MeOD): δ 7.28(m, 1H), 7.18(m, 1H), 7.04(m, 1H), 6.96 (m, 1H), 5.26(m, 1H), 3.73(m, 1H), 2.5(m, 1H), 2.19(m, 1H), 1.26 (m, 3H) | Described |
| 2 | (structure) | 373.20 [M + 1]; ¹H NMR(400 MHz, MeOD) δ 8.23(d, 1H, J=8.0Hz), 7.90(t, 1H, J=8.0Hz), 7.80(d, 1H, J=8.0Hz), 7.32(d, 1H, J=9.0Hz), 7.20(m, 2H), 7.05(d, 1H, J=9.0Hz), 7.01(t, 1H, J=8.0Hz), 4.77(s, 2H), 3.91 dd, 1H, J=6.6Hz, J=8.8Hz), 2.65(dd, 1H, J=6.6Hz, J=14.4Hz), 2.28(dd, 1H, J=8.8Hz,J=14.4Hz). | Described |
| 3 | (structure) | 317.10 [M + 1]; ¹H NMR(400 MHz, MeOD) δ 7.18(d, 1H, J=8.0Hz), 6.70(t, 1H, J=8.0Hz), 6.85(d, 1H, J=8.0Hz), 3.88(dd, 1H, J=9.0Hz,J=5.6Hz), 2.66(dd, 1H, J=5.6Hz, J=14.9Hz), 2.25(dd, 1H, J=9.0Hz, J=14.9Hz). | Described |
| 4 | (structure) | 255.1 [M + 1]; ¹H NMR(400 MHz, MeOD) δ 7.30(dd, 1H, J=1.29Hz,J=8.0Hz), 7.18, 9dt, 1H, J=1.3Hz, J=8.0Hz), 7.01 (dt, 1H, J=1.3Hz,J=8.0Hz), 6.95(dd, 1H, J=1.3Hz,J=8.0Hz), 4.74(d, 1H, J=3.80), 3.97(d, 1H, J=3.8). | Described |
| 5 | (structure) | 239.1 [M + 1]; ¹H NMR (400 MHz, MeOD): δ 8.48(s, 0.4H), 7.97(s, 0.6H), 7.49(m, 2H), 7.19(m, 2H, 4.03(m, 2H), 3.5(dd, 1H) | Described |

TABLE 1-continued

| Example | Compound | Physical Data<br>¹H NMR 400 MHz<br>(DMSO-d₆)<br>and/or MS (m/z) | Synthesis |
|---------|----------|-----------------------------------------------------------------|-----------|
| 6 | | 338.2 [M + 1] | Described |
| 7 | | 295.05 [M + 23]; ¹H NMR(400 MHz, MeOD): δ 8.95(s, 1H), 7.5(s, 1H), 7.3(d, 1H), 7.05(d, 1H), 4.35(s, 2H), 3.6(s, 2H) | Described |
| 8 | | 270.5 [M + 23] | Described |
| 9 | | 243.2 [M + 23] | Described |
| 10 | | 291.3 [M + 1]; 1H NMR (400 MHz, MeOD): δ 7.29(t, 1H), 7.20(d, 1H), 7.11(d, 1H), 7.04 (t, 1H), 3.97(m, 2H), 3.02-2.89(m, 2H), 2.77-2.65(m, 2H), 2.17 (dd, 1H), 1.65(m, 1H), 1.50(m, 2H), 0.97(2d, 6H). | Described |
| 11 | | 355.2 [M + 1]; ¹H NMR (400 MHz, MeOD): δ 8.30(dd, 1H), 8.04(d, 1H), 7.76(td, 1H), 7.24 (m, 2H), 7.12(dd, 1H), 7.05(t, 1H), 6.99(d, 1H), 4.91(d, 1H), 4.76 (d, 1H), 3.13(m, 1H), 3.03(dd, 1H), 2.90(dd, 1H), 2.73(dd, 1H), 2.25 (dd, 1H). | Described |

TABLE 1-continued

| Example | Compound | Physical Data<br>¹H NMR 400 MHz<br>(DMSO-d₆)<br>and/or MS (m/z) | Synthesis |
|---|---|---|---|
| 12 | | 235.3 [M + 1]; ¹H NMR(400 MHz, MeOD) δ 7.28(m, 2H), 7.17(dt, 1H, J=1.2Hz, J=8.0Hz), 7.04(dd, 1H, J=1.2Hz, J 8.0 Hz), 2.90(m, 2H), 2.72 (m, 1H), 2.55(m, 1H), 2.28(m, 1H), 2.15(m, 1H), 1.97(m, 1H). | Described |
| 13 | | 235.2 [M + 1]; ¹H NMR (400 MHz, MeOD): δ 8.13(s, 1H), 7.87(s, 1H), 7.17(m, 2H), 7.06 (t, 1H, J=8.0Hz), 6.92 (d, 1H, J=8.0Hz), 3.88 (dd, 1H, J=8.0Hz, J=14.4Hz), 3.24(dd, 1H, J=4.8Hz, J=14.4Hz), 2.77(m, 2H), 2.62(m, 1H), 2.11(m, 1H), 1.84 (m, 1H). | Described |
| 15 | | 296.2 [M + 1] | Synthesized as described for example 1, using bromo acetamide instead of 2-bromo propionamide. |
| 16 | | 278.2 [M + 1] | Synthesized as described for example 1, using bromo acetonitrile instead of 2-bromo propionamide. |
| 17 | | 275.0 [M + 23] | Synthesized as described for example 1. Using methyl iodide instead of 2-bromo propionamide. |
| 18 | | 315.05 [M + 23] | Synthesized as described for example 1, using (bromomethyl)cyclopropane instead of 2-bromo-propionamide. |

TABLE 1-continued

| Example | Compound | Physical Data ¹H NMR 400 MHz (DMSO-d$_6$) and/or MS (m/z) | Synthesis |
|---|---|---|---|
| 19 | (structure: 3,4-dihydro-1-benzyl-quinolin-2(1H)-one with N-hydroxyacetamide substituent) | 333.0 [M + 23] | Synthesized as described for example 10, using benzyl bromide instead of 1-bromo-3-methylbutane |
| 20 | (structure: 7-bromo-4H-benzo[1,4]thiazin-3-one with N-hydroxyacetamide substituent on N) | 339.0 [M + 23]; ¹H NMR (400 MHz, DMSO): δ 10.71(s, 1H), 8.93(s, 1H), 7.62 (d, J=2.2Hz, 1H), 7.344(dd, J=2.2,8.8, 1H), 6.99(d, J=8.8, 1H), 4.41(s, 2H), 3.56 (s, 2H) | Synthesized as described for example 3, using 7-bromo-4H-benzo[1,4]thiazin-3-one instead of 7-chloro-4H-benzo[1,4]thiazin-3-one. |
| 21 | (structure: benzo[1,4]thiazin-3-one with 2-methoxyethyl on N and N-hydroxyacetamide at C-2) | 297.33 [M + 1] | Synthesized as described for example 1, using 1-bromo-2-methoxyethane instead of 2-bromo propionamide. |
| 22 | (structure: benzo[1,4]thiazin-3-one with 3,3,3-trifluoropropyl on N and N-hydroxyacetamide at C-2) | 335.27 [M + 1] | Synthesized as described for example 1, using 3-bromo-1,1,1-trifluoropropane instead of 2-bromo propionamide. |
| 23 | (structure: benzo[1,4]thiazin-3-one with 3-methylbutyl on N and N-hydroxyacetamide at C-2) | 309.34 [M + 1] | Synthesized as described for example 1, using 1-bromo-3-methylbutane instead of 2-bromo propionamide. |
| 24 | (structure: benzo[1,4]thiazin-3-one with n-pentyl on N and N-hydroxyacetamide at C-2) | 309.2 [M + 1] | Synthesized as described for example 1, using 1-bromopentane instead of 2-bromo propionamide. |

TABLE 1-continued

| Example | Compound | Physical Data<br>¹H NMR 400 MHz<br>(DMSO-d₆)<br>and/or MS (m/z) | Synthesis |
|---|---|---|---|
| 25 | | 323.2 [M + 1] | Synthesized as described for example 1, using 1-bromo-4-methylpentane instead of 2-bromo propionamide. |
| 26 | | 243.15 [M + 23] | Synthesized as described in example 7 using 3,4-dihydroquinolin-2(1H)-one as a starting material instead of 7-chloro-4H-benzo[1,4]thiazin-3-one. |
| 27 | | 307.2 [M + 1]; ¹H NMR (400 MHz, CDCl₃): δ 7.38(1H, m),7.28-7.23 (1H, m), 7.15-7.13 (1H, m), 7.05-7.013 1H, m), 4.22-4.17(1H, m); 3.98-3.28(1H, m), 3.85-3.82(1H, m), 2.86-2.784(1H, m), 2.59-2.47(1H, m), 1.93-1.87(2H, m), 1.83-1.69(4H, m) | Synthesized as described for example 1, using (bromomethyl)cyclobutane instead of 2-bromo propionamide |
| 28 | | 371.2 [M + 1] | Synthesized as described for example 1, using 2-bromo-1-phenylpropan-1-one instead of 2-bromo propionamide. |
| 29 | | 337.4 [M + 1] | Synthesized as described for example 1, using 1-bromo-3,3-dimethylbutan-2-one instead of 2-bromo propionamide. |

TABLE 1-continued

| Example | Compound | Physical Data ¹H NMR 400 MHz (DMSO-$d_6$) and/or MS (m/z) | Synthesis |
|---|---|---|---|
| 30 | | 293.3 [M + 1] | Synthesized as described for example 1, using 4-bromobut-1-ene instead of 2-bromo propionamide. |
| 31 | | 335.2 [M + 1] | Synthesized as described for example 1, using (bromomethyl)cyclohexane instead of 2-bromo propionamide. |
| 32 | | 349.32 [M + 1] | Synthesized as described for example 1, using (2-(bromoethyl)cyclohexane instead of 2-bromo propionamide. |
| 33 | | 430.10 [M + 23] | Synthesized as described for example 2, using 3,4-difluorobenzenamine instead of 2-aminopyridine. |
| 34 | | 428.3 [M + 1]; ¹H NMR (400 MHz, DMSO): δ 10.82(s, 1H), 10.37(s, 1H), 9.2(bs, 1H), 7.50 (m, 7H), 5.05(dd, 2H), 4.25(m, 1H), 2.9(m, 1H), 2.74(q, 4H), 2.47 (m, 1H), 1.33(t, 6H) | Synthesized as described for example 2, using 2,6-diethylbenzenamine instead of 2-aminopyridine. |
| 35 | | 350.1 [M + 23] | Synthesized as described for example 2, using cyclopentylamine instead of 2-aminopyridine. |

TABLE 1-continued

| Example | Compound | Physical Data ¹H NMR 400 MHz (DMSO-d$_6$) and/or MS (m/z) | Synthesis |
|---|---|---|---|
| 36 | | 418.2 [M + 23] | Synthesized as described for example 2, using 1-(4-fluorophenyl)ethanamine instead of 2-aminopyridine. |
| 37 | | 275.3 [M + 1]; ¹H NMR (400 MHz, MeOD): δ 7.33-7.18(m, 3H), 7.04 (td, J=1.2,7.2Hz, 1H), 3.90(m, 2H), 3.06-2.90 (m, 2H), 2.81-2.65(m, 2H), 2.18(dd, J=8.2,14.8Hz, 1H), 1.15(m, 1H), 0.55-0.30(m, 4H). | Synthesized as described for example 10, using (bromomethyl)cyclopropane instead of 1-bromo-3-methylbutane. |
| 38 | | 422.2 [M + 1] | Synthesized as described for example 2, using (2,5-difluorophenyl)methanamine instead of 2-aminopyridine. |
| 40 | | 349.3 [M + 1]; ¹H NMR (400 MHz, MeOD): δ 7.29-7.18(m, 2H), 7.06 (t, J=7.2Hz, 1H), 6.95 (d, J=8.0Hz, 1H), 4.59 (m, 2H), 3.42(t, J=6.5Hz), 2H), 3.13(m, 1H), 3.03(dd, J=5.6,15.6Hz, 1H), 2.87(dd, J=11.6,15.4Hz, 1H), 2.66 (m, 3H), 2.43(s, 6H), 2.26(dd, J=8.0,14.7Hz, 1H). | Synthesized as described for example 11, using N¹,N¹-dimethylethane-1,2-diamine instead of 2-aminopyridine. |
| 41 | | 297.2 [M + 1]; ¹H NMR (400 Mhz, MeOD): δ 8.26(s, 0.4H), 7.73(s, 0.6H), 7.50(m, 1H), 7.33(m, 2H), 7.08(m, 1H), 4.1(m, 1H), 4.08 (m, 1H), 3.90(m, 1H), 3.66(m, 1H), 3.62(m, 3H), 3.30(s, 3H) | Synthesized in a similar way as described in example 6, using 1-bromo-2-methoxyethane instead of tert-butyl bromoacetate. |

TABLE 1-continued

| Example | Compound | Physical Data ¹H NMR 400 MHz (DMSO-$d_6$) and/or MS (m/z) | Synthesis |
|---|---|---|---|
| 42 | | 318.15 [M + 23] | Synthesized in a similar way as described in example 6, using 2-bromoacetamide instead of tert-butyl bromoacetate. |
| 43 | | 295.2 [M + 1] | Synthesized in a similar way as described in example 6, using n-butylbromide instead of tert-butyl bromoacetate. |
| 44 | | 293.2 [M + 1] | Synthesized in a similar way as described in example 6, using (bromomethyl)cyclopropane instead of tert-butyl bromoacetate. |
| 45 | | 309.2 [M + 1] | Synthesized in a similar way as described in example 6, using n-pentylbromide instead of tert-butyl bromoacetate. |
| 46 | | 329.2 [M + 1] | Synthesized in a similar way as described in example 6, using benzylbromide instead of tert-butyl bromoacetate. |

TABLE 1-continued

| Example | Compound | Physical Data ¹H NMR 400 MHz (DMSO-d$_6$) and/or MS (m/z) | Synthesis |
|---|---|---|---|
| 47 | | 365.0 [M + 23] | Synthesized as described for example 1, using 1-(2-bromoethyl)benzene instead of 2-bromo propionamide. |
| 48 | | 351.2 [M + 23] | Synthesized as described for example 1, using benzylbromide instead of 2-bromo propionamide. |
| 49 | | 339.2 [M + 1]; ¹H NMR (400 MHz, MeOD): δ 7.33(m, 3H), 7.09(m, 1H), 4.89(m, 1H), 4.13 (m, 2H), 3.85(m, 5H), 2.7(dd, 1H), 2.31(dd, 1H), 1.97(m, 2H) | Synthesized as described for example 1, using 2-(2-bromoethyl)-1,3-dioxolane instead of 2-bromo propionamide. |
| 50 | | 337.2 [M + 1] | Synthesized as described for example 1, using 2-(bromomethyl)-tetrahydro-2H-pyran instead of 2-bromo propionamide. |
| 51 | | 253.2 [M + 1]; ¹H NMR (400 MHz, MeOD): δ 7.24(m, 1H), 7.11(m, 1H), 6.91 (m, 2H), 3.77(m, 3H), 1.99(s, 3H) | Synthesized from 2-(benzyloxyamino-methyl)-4H-benzo[1,4]thiazin-3-one as described in example 5 using only Ac$_2$O. |
| 52 | | 347.2 [M + 1] | Synthesized in a similar way as described in example 6, using 1-(bromomethyl)-2-fluorobenzene instead of tert-butyl bromoacetate. |

TABLE 1-continued

| Example | Compound | Physical Data $^1$H NMR 400 MHz (DMSO-$d_6$) and/or MS (m/z) | Synthesis |
|---|---|---|---|
| 53 | (4-fluorobenzyl-substituted benzothiazinone N-hydroxyformamide) | 347.2 [M + 1] | Synthesized in a similar way as described in example 6, using 1-(bromomethyl)-4-fluorobenzene instead of tert-butyl bromoacetate. |
| 54 | (2,4-difluorobenzyl-substituted benzothiazinone N-hydroxyformamide) | 365.2 [M + 1] | Synthesized in a similar way as described in example 6, using 1-(bromomethyl)-2,4-difluorobenzene instead of tert-butyl bromoacetate. |
| 55 | (2-cyanobenzyl-substituted benzothiazinone N-hydroxyformamide) | 354.2 [M + 1] | Synthesized in a similar way as described in example 6, using 2-(bromomethyl)benzonitrile instead of tert-butyl bromoacetate. |
| 56 | (3-cyanobenzyl-substituted benzothiazinone N-hydroxyformamide) | 354.2 [M + 1] | Synthesized in a similar way as described in example 6, using 3-(bromomethyl)benzonitrile instead of tert-butyl bromoacetate. |

TABLE 1-continued

| Example | Compound | Physical Data ¹H NMR 400 MHz (DMSO-$d_6$) and/or MS (m/z) | Synthesis |
|---|---|---|---|
| 57 | | 354.2 [M + 1] | Synthesized in a similar way as described in example 6, using 4-(bromomethyl)benzonitrile instead of tert-butyl bromoacetate. |
| 58 | | 359.2 [M + 1] | Synthesized in a similar way as described in example 6, using 1-(bromomethyl)-3-methoxybenzene instead of tert-butyl bromoacetate. |
| 59 | | 382.2 [M + 1] | Synthesized in a similar way as described in example 6, using 4-(2-(bromoacetyl)benzonitrile instead of tert-butyl bromoacetate. |
| 60 | | 297.2 [M + 1] | Synthesized in a similar way as described in example 6. |

TABLE 1-continued

| Example | Compound | Physical Data ¹H NMR 400 MHz (DMSO-$d_6$) and/or MS (m/z) | Synthesis |
|---|---|---|---|
| 61 | | 387.2 [M + 1] | Synthesized in a similar way as described in example 6, using methyl 4-(bromomethyl)benzoate instead of tert-butyl bromoacetate. |
| 62 | | 373.2 [M + 1] | Synthesized in a similar way as described in example 6, using 3-aminopyridine instead of propylamine |
| 63 | | 349.3 [M + 1] | Synthesized in a similar way as described in example 6, using (2-(bromoethyl)cyclohexane instead of tert-butyl bromoacetate. |
| 64 | | 339.2 [M + 1] | Synthesized in a similar way as described in example 6, using 2-(2-bromoethyl)-1,3-dioxolane instead of tert-butyl bromoacetate. |

TABLE 1-continued

| Example | Compound | Physical Data<br>¹H NMR 400 MHz<br>(DMSO-d$_6$)<br>and/or MS (m/z) | Synthesis |
|---|---|---|---|
| 65 | | 379.3 [M + 1] | Synthesized in a similar way as described in example 6, using 1-bromo-3,7-dimethyloctane instead of tert-butyl bromoacetate. |
| 66 | | 309.2 [M + 1] | Synthesized in a similar way as described in example 6, using 1-bromobutan-2-one instead of tert-butyl bromoacetate. |
| 67 | | 341.2 [M + 1] | Synthesized in a similar way as described in example 6, using 1-(2-methoxyethoxy)-2-bromoethane instead of tert-butyl bromoacetate. |
| 68 | | 433.3 [M + 1] | Synthesized in a similar way as described in example 6, using 3-bromo-1,1-diphenylpropane instead of tert-butyl bromoacetate. |

TABLE 1-continued

| Example | Compound | Physical Data<br>¹H NMR 400 MHz<br>(DMSO-d₆)<br>and/or MS (m/z) | Synthesis |
|---|---|---|---|
| 69 | | 267.2 [M + 1] | Synthesized in a similar way as described in example 6, using ethylbromide instead of tert-butyl bromoacetate. |
| 70 | | 323.3 [M + 1] | Synthesized in a similar way as described in example 6, using 2-ethylbromobutane instead of tert-butyl bromoacetate. |
| 71 | | 299.2 [M + 1] | Synthesized in a similar way as described in example 6, using 3-fluoropropane instead of tert-butyl bromoacetate. |
| 72 | | 387.25 [M + 1] | Synthesized in a similar way as described in example 6, using 1-((3-bromopropoxy)methylbenzene instead of tert-butyl bromoacetate. |

TABLE 1-continued

| Example | Compound | Physical Data<br>¹H NMR 400 MHz<br>(DMSO-d₆)<br>and/or MS (m/z) | Synthesis |
|---------|----------|------------------------------------------------------------|-----------|
| 73 | | 387.3 [M + 1] | Synthesized in a similar way as described in example 6, using 1-(4-bromobutoxy)benzene instead of tert-butyl bromoacetate. |
| 74 | | 387.2 [M + 1] | Synthesized in a similar way as described in example 6, using 2-bromo-1-(3-methoxyphenyl)ethanone instead of tert-butyl bromoacetate. |
| 75 | | 387.2 [M + 1] | Synthesized in a similar way as described in example 6, using 2-bromo-1-(4-methoxyphenyl)ethanone instead of tert-butyl bromoacetate. |

TABLE 1-continued

| Example | Compound | Physical Data ¹H NMR 400 MHz (DMSO-$d_6$) and/or MS (m/z) | Synthesis |
|---|---|---|---|
| 76 | (structure shown) | 373.2 [M + 1] | Synthesized in a similar way as described in example 6, using 4-(bromomethyl)benzoic acid instead of tert-butyl bromoacetate. |
| 77 | (structure shown) | 412.2 [M + 1] | Synthesized in a similar way as described in example 6, using 2-(2-(bromoethyl)isoindoline-1,3-dione instead of tert-butyl bromoacetate. |
| 78 | (structure shown) | 365.3 [M + 1]; ¹H NMR (400 MHz, CDCl$_3$): δ 7.37(1H, dd, J=1.2Hz, 7.6Hz), 7.31-7.26 (1H, m), 7.14(1H, t, J=7.2Hz), 7.1-7.04 (1H, m), 4.06-3.56(4H, m), 1.62(2H, m), 1.25 (12H, m), 0.87(3H, t, J=6.8Hz) | Synthesized in a similar way as described in example 6, using 3-bromononane instead of tert-butyl bromoacetate. |

TABLE 1-continued

| Example | Compound | Physical Data ¹H NMR 400 MHz (DMSO-$d_6$) and/or MS (m/z) | Synthesis |
|---|---|---|---|
| 79 | | 339.2 [M + 1] | Synthesized in a similar way as described in example 6, using methyl 4-bromobutanoate instead of tert-butyl bromoacetate. |
| 80 | | 320.2 [M + 1] | Synthesized in a similar way as described in example 6, using 5-bromopentanenitrile instead of tert-butyl bromoacetate. |
| 81 | | 307.3 [M + 1] | Synthesized in a similar way as described in example 6, using 1-bromo-2-methylprop-1-ene instead of tert-butyl bromoacetate. |
| 82 | | 357.3 [M + 1] | Synthesized in a similar way as described in example 6, using 1-(3-bromopropyl)benzene instead of tert-butyl bromoacetate. |

TABLE 1-continued

| Example | Compound | Physical Data $^1$H NMR 400 MHz (DMSO-d$_6$) and/or MS (m/z) | Synthesis |
|---|---|---|---|
| 83 | 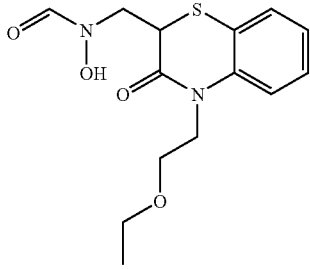 | 311.2 [M + 1]; $^1$H NMR (400 MHz, CDCl$_3$): δ 7.49(1H, dd, J=8Hz), 7.36(1H, m), 7.3-7.26 (1H, m), 7.07(1H, t, J=7.6Hz),4.24-4.17 (1H, m),4.13-4.032 (1H, m), 3.98-3.93(1H, m),3.86-3.78(1H, m), 3.77-3.61(3H, m), 3.582-3.48(2H, m), 1.19-1.16(3H, m) | Synthesized in a similar way as described in example 6, using 1-bromo-2-ethoxyethane instead of tert-butyl bromoacetate. |
| 84 | 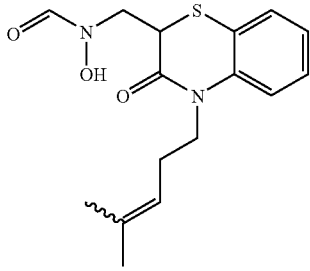 | 321.3 [M + 1]; $^1$H NMR (400 MHz, CDCl$_3$): δ 7.37(1H, dd, J=1.2Hz, 7.6Hz), 7.31-7.26(1H, m), 7.17(1H, t, J=7.2Hz), 7.08-7.04 (1H, m), 5.08(1H, d, J=5.2Hz ), 4.06-3.55 (5H, m), 2.29(2H, q, J=7.6Hz), 1.67(3H, s), 1.53(3H, s) | Synthesized in a similar way as described in example 6, using 5-bromo-2-methylpent-2-ene instead of tert-butyl bromoacetate. |
| 85 | 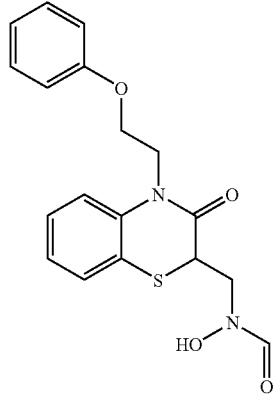 | 359.2 [M + 1]; $^1$H NMR (400 MHz, CDCl$_3$): δ 7.56(1H, dd, J=8Hz), 7.39-7.24(4H, m), 7.11-7.07(1H, m), 6.98-6.93(1H, m), 6.87 (2H, dd, J=8.4Hz, 1.4Hz), 4.43-4.21(4H, m), 4.08-3.53(2H, m) | Synthesized in a similar way as described in example 6, using 1-(2-bromoethoxy)benzene instead of tert-butyl bromoazetate. |
| 86 | 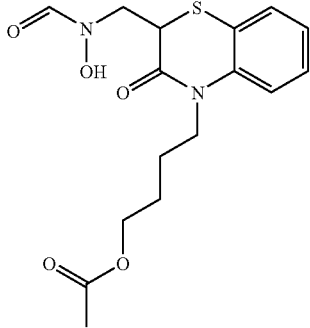 | 353.2 [M + 1] | Synthesized in a similar way as described in example 6, using 4-bromobutyl acetate instead of tert-butyl bromoacetate. |

TABLE 1-continued

| Example | Compound | Physical Data<br>$^1$H NMR 400 MHz<br>(DMSO-$d_6$)<br>and/or MS (m/z) | Synthesis |
|---|---|---|---|
| 87 | | 367.3 [M + 1]; $^1$H NMR (400 MHz CDCl$_3$): δ 7.43-7.31(3H, m), 7.15-7.05(1H, m), 4.12-4.05(4H, m), 3.93-3.77(2H, m), 2.34 (2H, t, J=6.8Hz), 1.69-1.61 (4H, m), 1.22(3H, t, J=7.2Hz) | Synthesized in a similar way as described in example 6, using ethyl 5-bromopentanoate instead of tert-butyl bromoacetate. |
| 88 | | 323.3 [M + 1]; $^1$H NMR (400 MHz, CDCl$_3$): δ 7.37(1H, dd, J=1.2Hz,7.6Hz), 7.31-7.26 (1H, m), 7.14(1H, t, J=7.2Hz), 7.08-7.04 (1H, m), 4.06-3.54(4H, m), 1.604(2H, m), 1.29 (6H, m), 0.87(3H, t, J=6.4Hz) | Synthesized in a similar way as described in example 6, using n-bromohexane instead of tert-butyl bromoacetate. |

The compounds of the invention, e. g. the compounds of formula I in free form or in pharmaceutically acceptable salt form or a prodrug thereof, exhibit valuable pharmacological properties, e.g. as anti-infectious agents, e.g. as indicated by the in vitro test given in Example 3 and are therefore indicated for therapy.

Example 14

Inhibition of Peptide Deformylase Activity

PDF assays with the S. aureaus enzyme are performed in duplicate according to Clements et al. (Antimicrob. Agents Chemother. 2001, 45, 563-570) using f-Met-Ala-Ser (f-MAS) as substrate and detecting the free amino group of the PDF product MAS with fluorescamine. Assays are performed in 384 well plates with a final well volume of 50 µl containing 5 nM PDF, 2 mM f-MAS, 80 mM HEPES (pH7.4), 0.7M KCl, 1 mM NiCl$_2$, 0.135% Brij35, and 1.25 mM TCEP. The reaction mix is incubated for 30 minutes with various concentrations of the inhibitor at room temperature and the free amino group of the substrate MAS is detected by the addition of 25 µl of 0.2 mg/ml fluorescamine in acetonitrile. Fluorescence is quantified with an Acquest plate reader using an excitation wavelength of 388 nm and an emission wavelength of 445 nm. Assay controls of plus or minus enzyme provide the 0 and 100% inhibition values, respectively. Analysis of the data is done by conversion of the fluorescence units to percent inhibition and the data is plotted against percent inhibition. The concentration (nanomolar) of inhibitor required to decrease enzyme activity by 50% (IC50) is determined from a dose response curve.

The compounds of Formula I in free form or in pharmaceutically acceptable salt form, exhibit valuable pharmacological properties, e.g. antibacterial properties, for example, as indicated by the in vitro tests of Example 4 and are therefore indicated for therapy. The compounds of the invention exhibit inhibitory activity for PDF with an IC$_{50}$ in the range of $1 \times 10^{-9}$ to $1 \times 10^{-5}$ M, preferably less than 500 nM, more preferably less than 100 nM. For example, N-hydroxy-2-(3-oxo-3,4-dihydro-2H-benzo[1,4]thiazin-2-yl)-acetamide (Example 1) has an IC50 of less than 5 nM.

The compounds of the present invention are, therefore, useful for the treatment and/or prevention of infectious disorders caused by a variety of bacterial or prokaryotic organisms.

Examples include, but are not limited to, Gram positive and Gram negative aerobic and anaerobic bacteria, including: Staphylococci, e.g. S. aureus and S. epidertnidis; Enferococci, e.g. E. faecalis and E. faecium; Streptococci, e.g. S. pneumoniae; Haemophilus, e.g. H. influenza; Moraxella, e.g. M. catarrhalis; Bacteroides, e.g. Bacteroides fragilis, Clostridium, e.g. Clostridium difficile; Niesseria, e.g. M. meningitides and N. gonorrhoae, Legionella, and Escherichia, e. g. E. coli. Other examples include Mycobacteria, e.g., M tuberculosis; intercellular microbes, e.g. Chlamydia and Rickettsiae; Mycoplasma, e.g. M. pneumoniae; Pseudomonas, e.g. P. aeruginosa; Helecobacter Pylori; and parasites, e.g. Plasmodium falciparum.

As used herein, an "infectious disorder is any disorder characterized by the presence of a microbial infection, such as the presence of bacteria. Such infectious disorders include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g. arteriosclerosis.

The compounds may be used to treat a subject to treat, prevent, and/or reduce the severity of an infection. Subjects include animals, plants, blood products, cultures and surfaces such as those of medical or research equipment, such as glass, needles, surgical equipment and tubing, and objects intended for temporary or permanent implantation into an organism.

Preferred animals include mammals, e.g. mice, rats, cats, dogs, cows, sheep, pigs, horses, swine, primates, such as rhesus monkeys, chimpanzees, gorillas, and most preferably humans. Treating a subject includes, but is not limited to, preventing, reducing, and/or eliminating the clinical symptoms caused by an infection of a subject by a microorganism; preventing, reducing, and/or eliminating an infection of a subject by a microorganism; or preventing, reducing, and/or eliminating contamination of a subject by a microorganism. The microorganism involved is preferably a prokaryote, more preferably a bacterium.

For the above uses the required dosage will of course vary depending on the mode of administration, the particular condition to be treated and the effect desired. The compositions may contain, for example, from about 0.1% by weight to about 99% by weight, e. g. from about 10-60% by weight, of the active material, depending on the method of administration.

Where the compositions comprise dosage units, each unit will contain, for example, from about 1-1000 mg, e.g. 1-500 mg, of the active ingredient. The dosage as employed for adult human treatment will range, for example, from about 1-3000 mg per day, for instance 1500 mg per day depending on the route and frequency of administration. Such a dosage corresponds to about 0.015-50 mg/kg per day. Suitably the dosage is, for example, from about 5-20 mg/kg per day. Suitable unit dosage forms for oral administration comprise ca. 0.25-1500 mg active ingredient.

The compounds of Formula I can be administered by any conventional route, e.g. locally or systemically e.g. orally, topically, parenterally, subdermally or by inhalation and may be used for the treatment of bacterial infection in a subject such as animals, preferably, mammals, more preferably, humans.

Pharmaceutical compositions comprising a compound of Formula I in free form or in pharmaceutically acceptable salt form in association with at least one pharmaceutical acceptable carrier or diluent can be manufactured in conventional manner by mixing with a pharmaceutically acceptable carrier or diluent. A "pharmaceutically acceptable carrier" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable carriers used in the specification and claims includes both one and more than one such carriers.

The compounds of the invention may be formulated for administration in any convenient way for use in human or veterinary medicine, by analogy with other antibiotics. Such methods are known in the art (see, e. g. Remington's Pharmaceutical Sciences, Easton, Pa.: Mack Publishing Co.) and are not described in detail herein.

The compositions may be in any form known in the art, including but not limited to tablets, capsules, wafers, fast melts (without wafers), powders, granules, lozenges, creams or liquid preparations, such as oral or sterile parenteral solutions or suspensions. The compounds may also be administered in liposomal, micellar or emulsion formulations. The compounds may also be administered as prodrugs, where the prodrug administered undergoes biotransformation in the treated mammal to a form that is biologically active.

The topical formulations of the present invention may be presented as, for instance, ointments, creams or lotions, solutions, salves, emulsions, plasters, eye ointments and eye or ear drops, impregnated dressings, transdermal patches, sprays and aerosols, and may contain appropriate conventional additives such as preservatives, solvents to assist drug penetration and emollient in ointments and creams.

The formulations may also contain compatible conventional carriers, such as cream or ointment bases and ethanol or oleyl alcohol for lotions. Such carriers may be present, for example, from about 1% up to about 99% of the formulation. For example, they may form up to about 80% of the formulation.

Tablets and capsules for oral administration may be in unit dose presentation form, and may contain conventional excipients such as binding agents, for example, syrup, acacia, gelatin, sorbitol, tragacanth, or polyvinylpyrollidone; fillers, for example, lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents, such as sodium lauryl sulphate. The tablets may be coated according to methods well-know in standard pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats; emulsifying agents, for example, lecithin, sorbitan monooleate or acacia; non-aqueous vehicles (which may include edible oils), for example, almond oil, oily esters such as glycerine, propylene glycol, or ethyl alcohol; preservatives, for example, methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, may be either suspended or dissolved in the vehicle or other suitable solvent. In preparing solutions, the compound may be dissolved in water for injection and filter sterilized before filling into a suitable vial or ampule and sealing. Advantageously, agents such as a local anesthetic preservative and buffering agents may be dissolved in the vehicle. To enhance the stability, the composition may be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound may be sterilized by exposure to ethylene oxide before suspending in the sterile vehicle. Advantageously, a surfactant or wetting agent is included in the composition to facilitate uniform distribution of the compound.

The compounds of the invention, e. g. the compounds of formula I, may be administered in free form or in pharmaceutical acceptable salt form e. g. as indicated above. Such salts may be prepared in conventional manner and exhibit the same order of activity as the free compounds.

In accordance with the foregoing the present invention further provides:

1.1 A method for treating and/or preventing an infectious disorder in a subject, such as a human or other animal subject, comprising administering to the subject an effective amount of a compound of the invention, e. g. of formula I, a pharmaceutically acceptable salt thereof or a prodrug thereof.

1.2 A method for inhibiting peptidyl deformylase in a subject comprising administering to the subject an effective peptidyl deformylase inhibiting amount of a compound of the invention, e. g. of formula 1, a pharmaceutical acceptable salt thereof or a prodrug thereof.

2. A compound of the invention, e. g. of formula I, in free form or in a pharmaceutical acceptable salt form for use as a pharmaceutical, e. g. in any method as indicated under 1.1 or 1.2 above.

3. A pharmaceutical composition, e. g. for use in any of the methods as in 1.1 or 1.2 above comprising a compound of the invention, e. g. of formula I, in free form or pharmaceutical acceptable salt form e. g. in association with a pharmaceutically acceptable diluent or carrier therefor.

4. A compound of the invention, e. g. of formula I, a pharmaceutically acceptable salt or a prodrug thereof for use as a pharmaceutical or in the preparation of a pharmaceutical composition for use in any method as indicated under 1.1 or 1.2 above.

"Treating" or "treatment of" a disease includes: (1) preventing the disease, i.e. causing the clinical symptoms of the disease not to develop in a subject, e. g. a mammal, that may be exposed to or predisposed to the disease but does not yet experience or display symptoms of the disease, (2) inhibiting the disease, i. e. arresting or reducing the development of the disease or its clinical symptoms, or (3) relieving the disease, i. e. causing regression of the disease or its clinical symptoms.

"Effective peptidyl deformylase inhibiting amount" means the amount of a compound, a pharmaceutically acceptable salt thereof or a prodrug thereof, that when administered to a subject for treating an infectious disorder responsive to inhibition of peptidyl deformylase or for inhibiting peptidyl deformylase, is sufficient to inhibit peptidyl deformylase. The "effective peptidyl deformylase inhibiting amount will vary depending on the compound, salt thereof or prodrug thereof, employed, the microorganism that is inhibited in the subject, the age, weight, sex, medical condition, species, disorder and its severity, of the subject to be treated, and the route of administration, but may nevertheless be readily determined by one skilled in the art.

The compounds of the invention, e. g. of formula 1, a pharmaceutically acceptable salt thereof or prodrug thereof, may be administered alone or in combination with another therapeutic agent. Examples of such therapeutic agents include, but are not limited to, other antibacterial agents such as β-lactams, e.g. penicillins; cephalosporins; carbapenems; ketolides; quinolones e.g. fluoroquinolones; macrolides, e.g. clarithromycin, azithromycin or vancomycin; rifamycins; monobactams; isoniazid; licosamides; mupirocin; sulfonamides; phenicols; fosfomycin; glycopeptides; tetracyclines; streptogramins; chloramphenicol; and oxazolidinone, anti-inflammatory agents, e.g. corticosteroids or NSAID, analgesics, e.g. narcotic or non-opioic analgesics.

In accordance with the foregoing the present invention provides in a yet further aspect:

5. A method as defined above comprising co-administration, e. g. concomitantly or in sequence, of a therapeutical effective amount of a compound of the invention, e. g. of formula I, a pharmaceutical acceptable salt thereof or a prodrug thereof, and a second therapeutic agent.

6. A therapeutic combination, e.g. a kit, comprising a) a compound of the invention, e.g. of formula I, a pharmaceutically acceptable salt thereof or a prodrug thereof, and b) at least one second therapeutic agent. Component a) and component b) may be used concomitantly or in sequence. The kit may comprise instructions for its administration.

The following are representative pharmaceutical formulations containing a compound of formula I.

Tablet Formulation

The following ingredients are mixed intimately and pressed into single scored tablets:

| Quantity per Ingredient | Tablet (mg) |
|---|---|
| Compound of this invention | 400 |
| Cornstarch | 50 |
| Croscarmalose sodium | 25 |
| Lactose | 120 |
| Magnesium stearate | 5 |

Capsule Formulation

The following ingredients are mixed intimately and loaded into a hard-shell gelatin capsule:

| Quantity per Ingredient | Capsule (mg) |
|---|---|
| Compound of this invention | 200 |
| Lactose, spray--dried | 148 |
| Magnesium stearate | 2 |

Suspension Formulation

The following ingredients are mixed to form a suspension for oral administration:

| Ingredient | Amount | |
|---|---|---|
| Compound of this invention | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.0 | g |
| Sorbitol (70% solution) | 13.00 | g |
| Veegum K (Vanderbilt Co.) | 1.0 | g |
| Flavoring | 0.035 | ml |
| Colorings | 0.5 | mg |
| Distilled water | q.s. to 100 | ml |

Injectable Formulation

The following ingredients are mixed to form an injectable formulation:

| Ingredient | Amount |
| --- | --- |
| Compound of this invention | 0.2-20 mg |
| Sodium acetate buffer solution, .4 M | 20 ml |
| HCl (1N) or NaOH (1N) | q.s. to suitable pH |
| Water (distilled, sterile) | q.s. to 20 ml |

Suppository Formulation

A suppository of total weight 2.5 g is prepared by mixing the compound of the invention with Witepsol® H-5 (triglycerides of saturated vegetable fatty acid; Riches-Nelson, Inc., New York), and has the following composition:

| Compound of the invention | 500 mg |
| --- | --- |
| Witepsol® | 2000 mg |

The compounds of the invention are useful to inhibit bacteria wherever it is desired to inhibit bacteria by contacting the bacteria with one or more compounds of the invention. Because of their ability to inhibit bacteria, the compounds of the invention are particularly useful to prevent contamination of cell cultures. As used in this context, the term "inhibit" means the suppression, control, stasis, or kill of bacteria.

Eukaryotic cells, in particular animal cells, are often cultured for various reasons such as for their ability to produce substances such as proteins. Examples of such cells include Chinese hamster ovary cells (CHO cells), African green monkey kidney cells, hybridomas constructed by fusing a parent cell (myeloma, etc.) with a useful substance-producing normal cell (lymphocyte, etc.), and the like. Typically, the compounds of the invention are incorporated into cell culture media at a bacteria inhibiting amount, e.g., a concentration of about 0.0001 to about 10 preferably about 0.0001 to about 1 microgram/ml, and more preferably about 0.001 to about 0.1. Any conventional cell culture medium known in the art can be used.

In accordance with the foregoing the present invention provides in a yet further aspect:

7. A method for preventing bacterial contamination of a cell culture medium comprising incorporating into said cell culture medium a bacteria inhibiting amount of a compound of the invention, e.g. of formula or a acceptable salt thereof. 8. A cell culture medium comprising a bacteria inhibiting amount of a compound of the invention, e.g. of formula or an acceptable salt thereof.

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

We claim:
1. The compounds selected from:

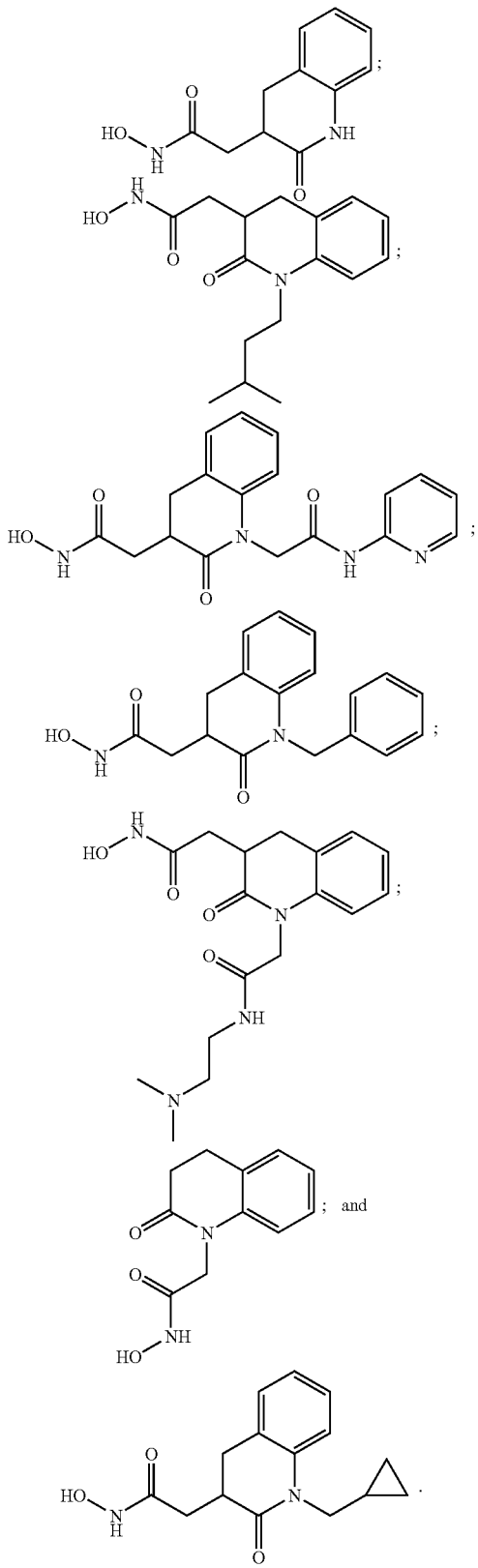

* * * * *